(12) United States Patent
Koch et al.

(10) Patent No.: US 12,099,180 B2
(45) Date of Patent: *Sep. 24, 2024

(54) ERGONOMIC EZ SCOPE DIGITAL IMAGING SYSTEM

(71) Applicant: KGG INC, Rochester, VT (US)

(72) Inventors: Anne Lauren Koch, Palm Beach Gardens, FL (US); Walter Golub, Rochester, VT (US); John Gatti, Lees Summit, MO (US); Bryce Rutter, Creve Coeur, MO (US); Anthony Ledwon, St. Charles, MO (US); B Cooper Priess, St. Louis, MO (US)

(73) Assignees: Anne Koch, Palm Beach Gardens, FL (US); Walter Golub, Rochester, VT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/882,275

(22) Filed: Aug. 5, 2022

(65) Prior Publication Data

US 2022/0369914 A1 Nov. 24, 2022

Related U.S. Application Data

(62) Division of application No. 17/244,179, filed on Apr. 29, 2021, now Pat. No. 11,448,868.

(Continued)

(51) Int. Cl.
*G02B 23/18* (2006.01)
*A61B 1/00* (2006.01)
(Continued)

(52) U.S. Cl.
CPC .......... *G02B 23/18* (2013.01); *A61B 1/00052* (2013.01); *A61B 1/00149* (2013.01);
(Continued)

(58) Field of Classification Search
CPC ........ G02B 23/18; G02B 7/06; G02B 21/008; G02B 21/362; G02B 21/365; G02B 21/368; G02B 21/0012; A61B 1/00052; A61B 1/00149; A61B 1/06; A61B 1/24; A61B 90/361; A61B 90/50; G03B 17/561;
(Continued)

(56) References Cited

U.S. PATENT DOCUMENTS 11,448,868 B2 * 9/2022 Koch ..................... H04N 23/65

* cited by examiner

*Primary Examiner* — Gevell V Selby
(74) *Attorney, Agent, or Firm* — Alfred M. Walker; John F. Vodapic

(57) ABSTRACT

An ergonomic digital imaging system obviates the need for, and replaces, the standard microscope with binoculars for viewing images, thereby freeing the user from using his or her hands to manipulate images seen through the binoculars of the microscope, whereby the user can use his or her hands for other tasks, such as dental or other surgery, from a position away from the exhaled breath of the patient being treated. The images are maintained focused, no matter how close or far the viewer is to the viewing display screen. The system is collapsible and portable, so that specialists can take the system from office to office, a plug and play work environment. The extended maneuverability of the camera head results in simple and fast patient positioning, and the camera and display module adjust for any comfortable sit or stand ergonomics of the practitioner.

23 Claims, 21 Drawing Sheets

Related U.S. Application Data

(60) Provisional application No. 63/144,942, filed on Feb. 2, 2021, provisional application No. 63/021,486, filed on May 7, 2020.

(51) Int. Cl.
| | | |
|---|---|---|
| *A61B 1/06* | (2006.01) | |
| *A61B 1/24* | (2006.01) | |
| *A61B 90/00* | (2016.01) | |
| *A61B 90/50* | (2016.01) | |
| *G02B 7/06* | (2021.01) | |
| *G03B 17/56* | (2021.01) | |
| *H04N 23/63* | (2023.01) | |
| *H04N 23/65* | (2023.01) | |
| *H04N 23/67* | (2023.01) | |
| *H04N 23/69* | (2023.01) | |
| *H04N 23/695* | (2023.01) | |

(52) U.S. Cl.
CPC .................. *A61B 1/06* (2013.01); *A61B 1/24* (2013.01); *A61B 90/361* (2016.02); *A61B 90/50* (2016.02); *G02B 7/06* (2013.01); *G03B 17/561* (2013.01); *H04N 23/632* (2023.01); *H04N 23/65* (2023.01); *H04N 23/67* (2023.01); *H04N 23/69* (2023.01); *H04N 23/695* (2023.01)

(58) Field of Classification Search
CPC ...... H04N 23/632; H04N 23/65; H04N 23/67; H04N 23/69; H04N 23/695; H04N 23/675
See application file for complete search history.

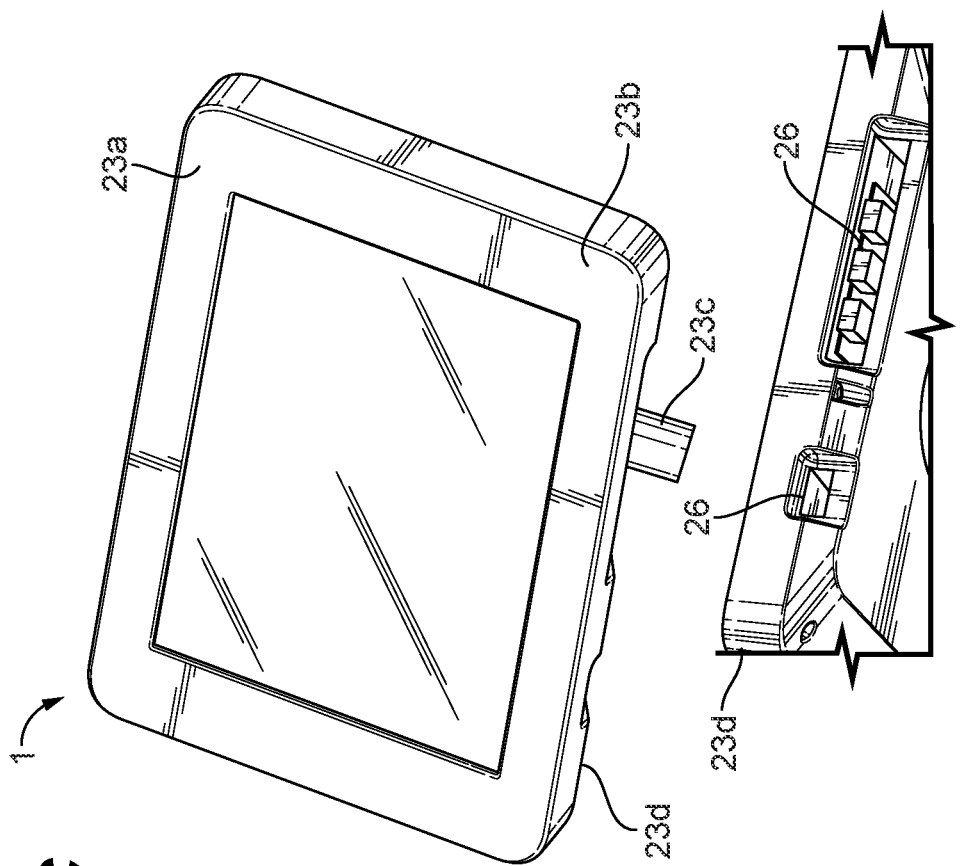
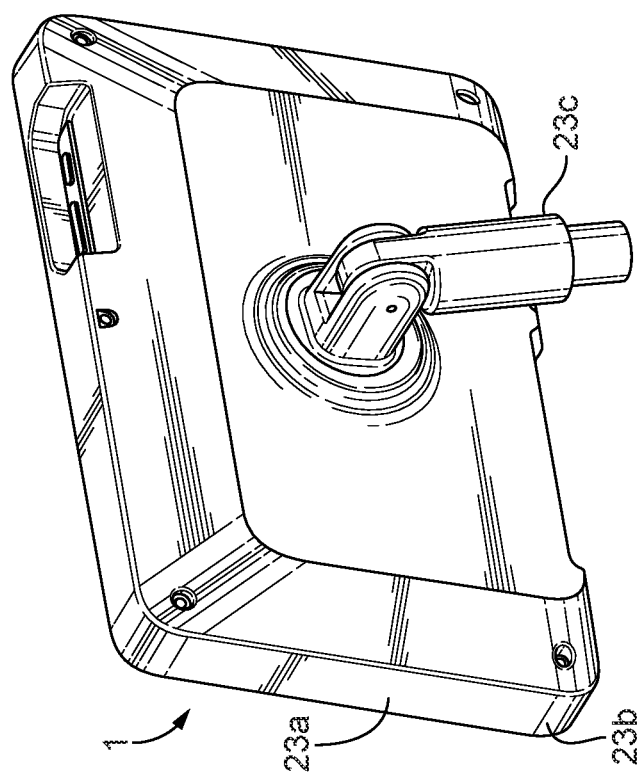
*FIG. 3C*
*FIG. 3D*
*FIG. 3B*

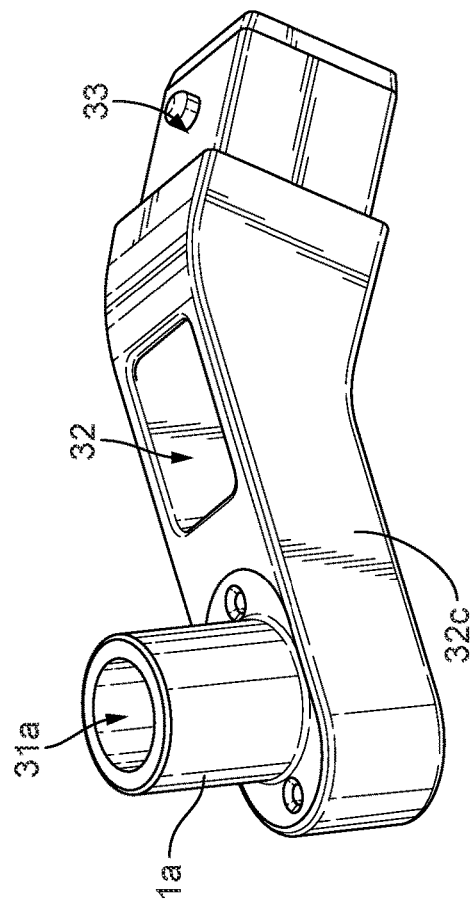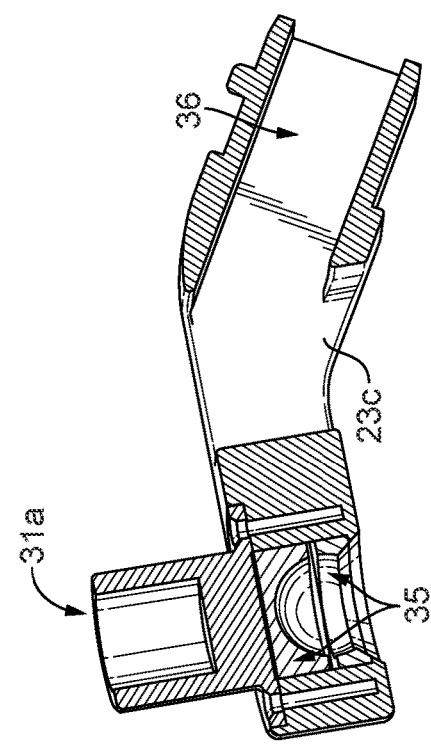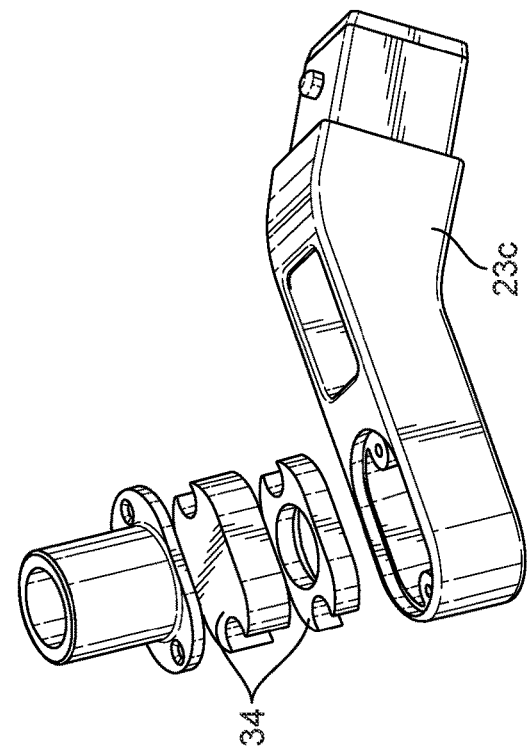
FIG. 4A
FIG. 4C
FIG. 4B

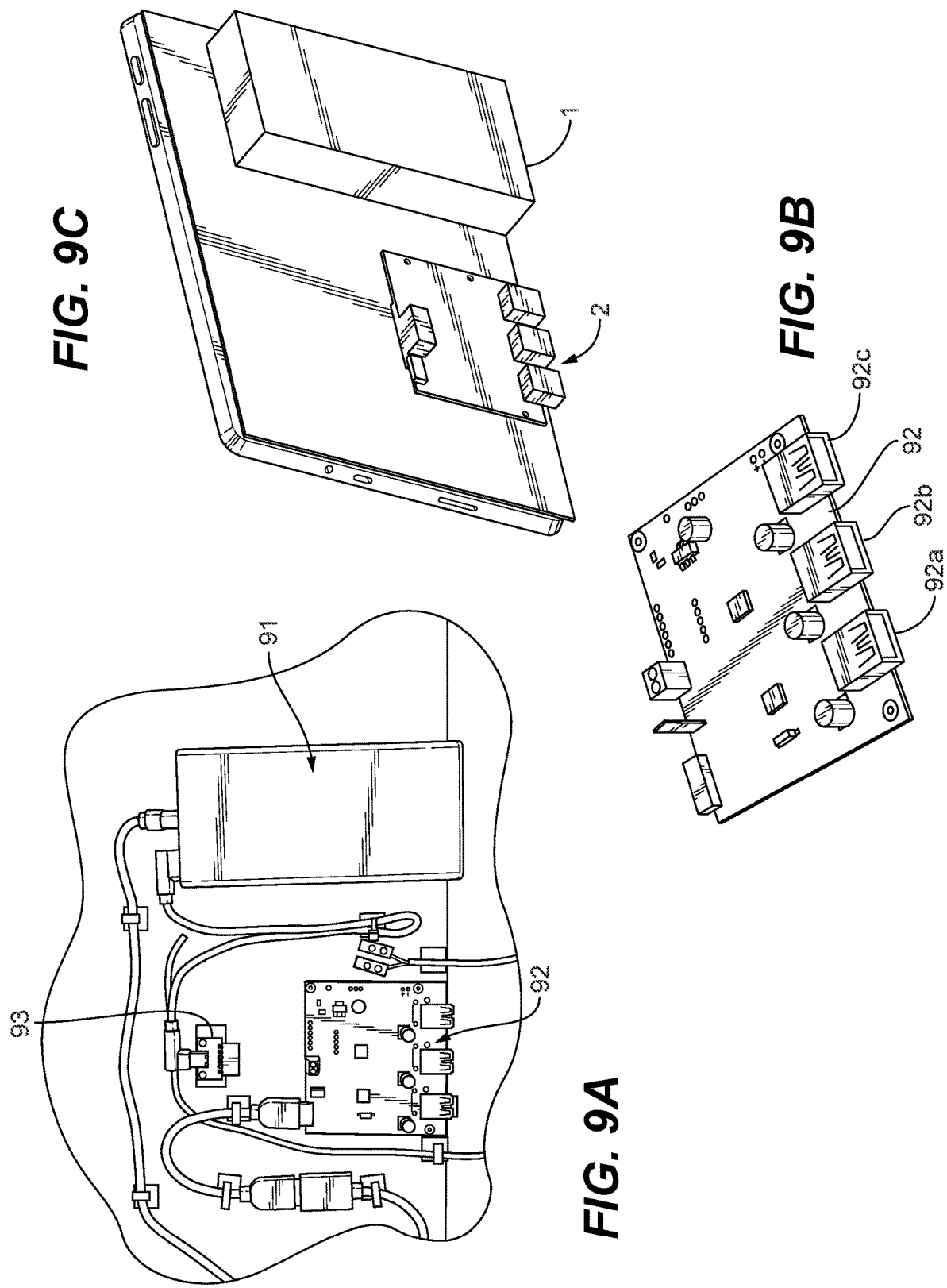

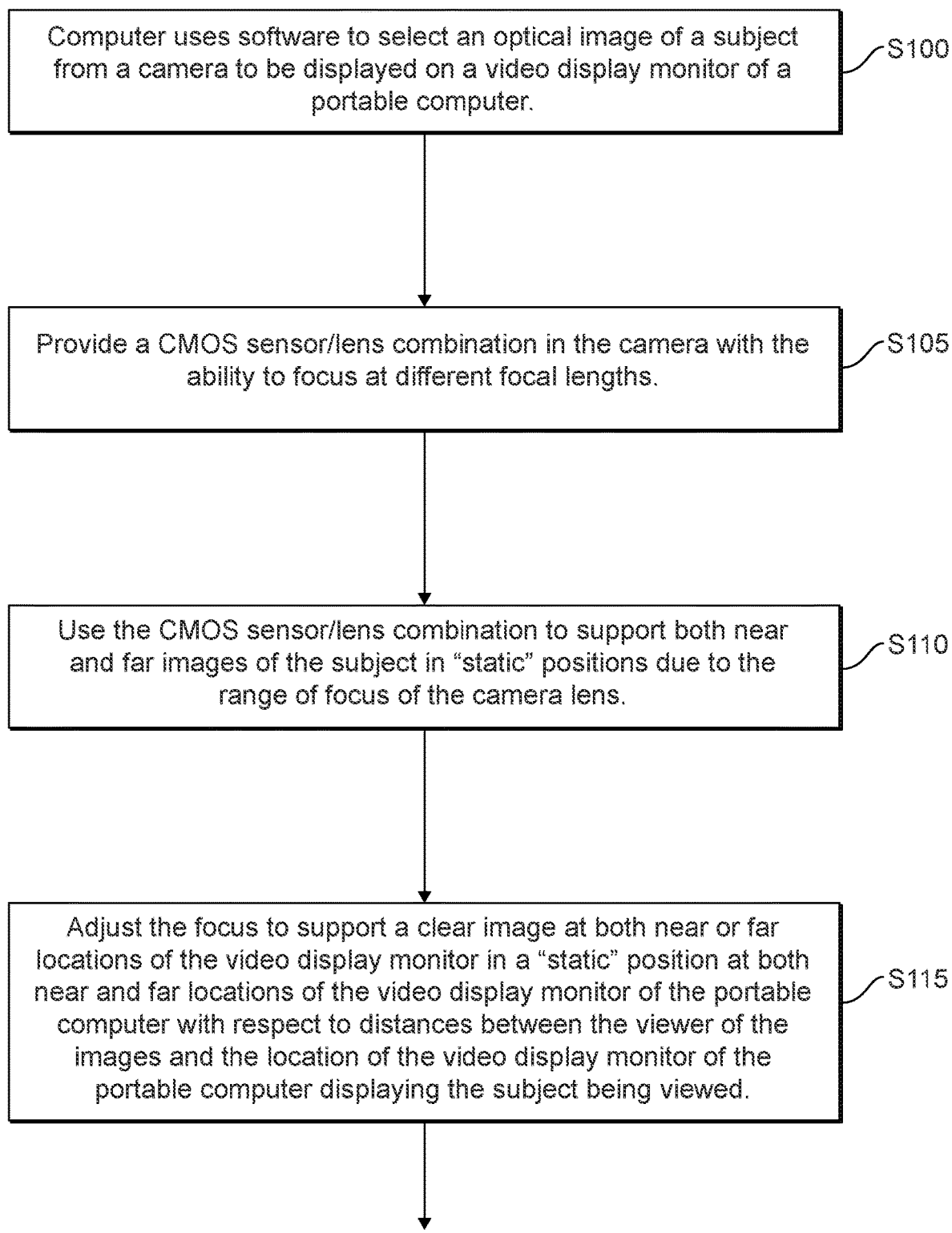

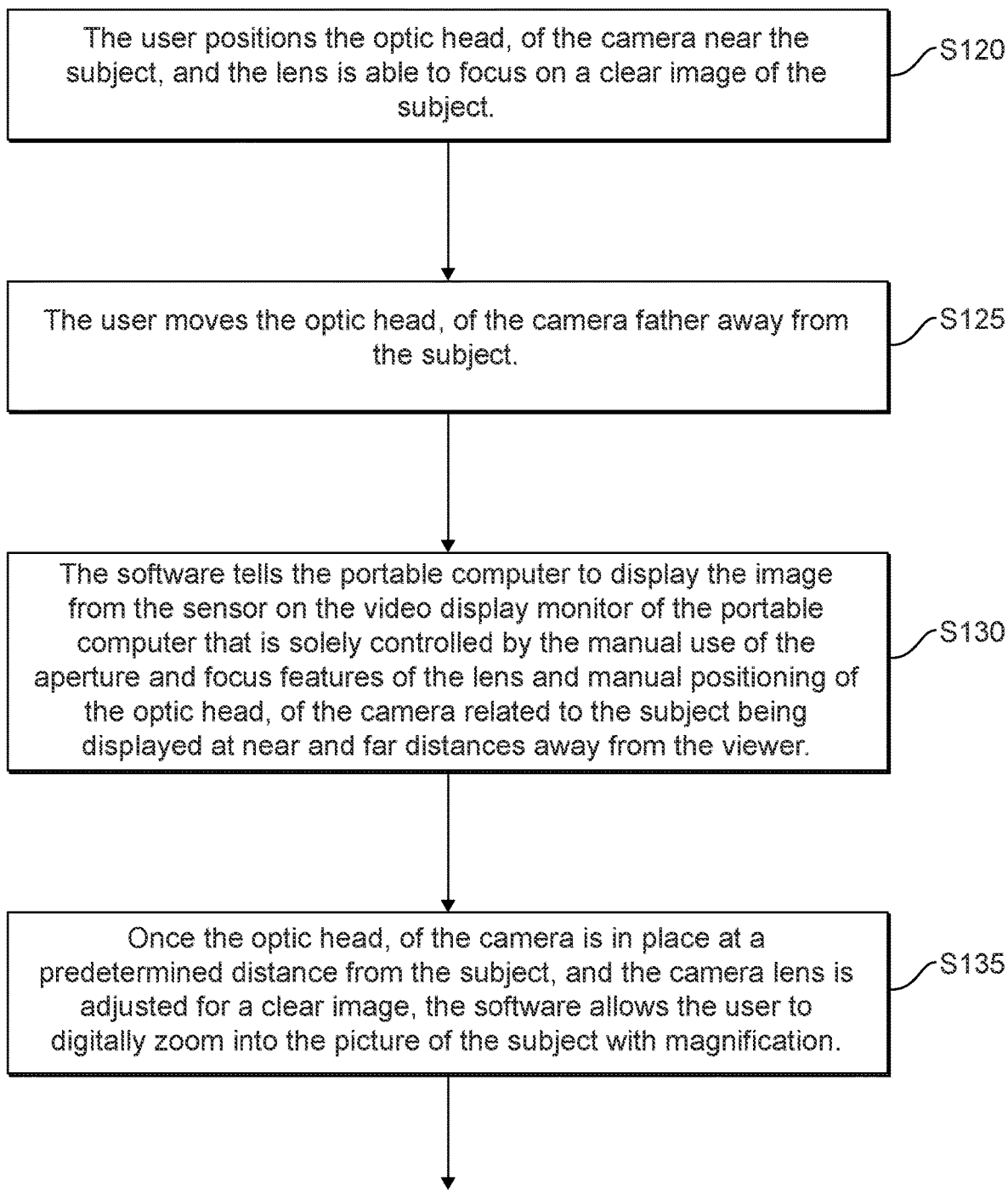

ERGONOMIC EZ SCOPE DIGITAL IMAGING SYSTEM

CROSS-REFERENCE TO RELATED APPLICATIONS

This application is a divisional of application Ser. No. 17/244,179, filed Apr. 29, 2021 and claims priority under 35 USC § 120 therefrom, the content of which '179 application is incorporated herein by reference. This application also derives the benefit of the filing date of U.S. Provisional Patent Application No. 63/144,942, filed Feb. 2, 2021, (the '942 application) and of U.S. Provisional Patent Application No. 63/021,486, filed May 7, 2020 (the '486 application) the content of which provisional '942 and '486 applications are incorporated herein by reference.

FIELD OF THE INVENTION

The present invention relates to a digital imaging system that obviates the need for, and replaces, the standard microscope with binoculars for viewing images, thereby freeing the user from using his or her hands to manipulate images seen through the binoculars of the microscope, whereby the user can use his or her hands for other tasks, such as dental or other surgery, from a position away from the exhaled breath of the patient being treated. Similarly, the present invention obviates the need for, and replaces, standard loupes, thereby eliminating constant changes in the focal length of the user's sightline when going between loupes and direct vision, effectively eliminating eye fatigue as a result of this use scenario.

BACKGROUND OF THE INVENTION

The use of enhanced magnification and light is still very limited in dentistry. Studies put the use of microscopes in dentistry at less than 2% of practicing dentists. Lack of ease of use, cost, physical size, and physical discomfort as a result of putting users in compromised ergonomic postures were all seen as reasons not to employ the use of a microscope. Clearly the biggest challenge was lack of ease of use and physical discomfort.

Among known dental microscopic devices include U.S. Pat. No. 7,860,289 of Yoo et al for a dental microscope system with one or more displays for displaying a microscopic image from an image data processing device. In contrast to Yoo '289, the present invention is an ergonomic, versatile, totally mobile system independent of the host organization's computer network and management systems. Its essential components can be moved from office to office and can be used with a custom designed arm for medical/dental purposes or set on a fixed base for industrial microscopy and for manufacturing quality control inspections, which allows complete freedom of movement in all directions and easy and simple magnification control.

Other prior art patents include European Patent Application number 0175549 A2 to Palcic et al., which discloses a dynamic microscope image processing scanner, which scans microscopic objects under the microscope. The images are digitized by a sensor and viewed by a camera and processed with a digital signal processor, and location coordinates of the objects are identified and viewed on a remote image display screen.

Additionally, Palcic et al '549, describes a conventional microscope with a motor driven stage (platform) that provides microscopic scans, on the cellular level, along both an X-axis and a Y-axis. In contrast to Palcic et a '549, the present invention is not a conventional microscope and does not utilize eyepieces, a beam splitter or camera ports. The image sensor that Palcic et al. '549, describe is mounted on a camera port, which is instead a component of certain surgical operating microscopes. Furthermore, the signals from the Palcic et al '549 sensor are sent to an external computer for storage and processing. This is different from the present invention, wherein image capture, processing, and storage is accomplished by the software associated with the ergonomic image display system of the present invention itself.

The U.S. Pat. No. 6,611,278 of Rosenfeld is an example with flow charts of computer software transforming image data to make animated cartoon characters images appear more life-like when talking. See *McRO, Inc. v. Bandai Namco Games America, Inc.*, et al. (*Fed. Cir.* 2016), which upheld the '278 patent of Rosenfeld under 35 USC § 101.

On May 5, 2020, inventors herein, Dr. Anne Lauren Koch, Dr. John Gatti and Dr. Walter Golub filed provisional patent application No. 63/021,486, entitled "EZ Scope™". The subject matter of that provisional patent application '486 removed the use of binocular eyepieces and has instead placed a touchscreen high-definition monitor for viewing purposes. When designing the original EZ Scope™ provisional patent application '486, it became apparent that with the improvement in digital technology, a digital version could be instructed to use all the advantages associated with digital technology rather than employing analog technology. The result is a fully functioning "digital imaging system" built on digital technology and software, with a touchscreen user interface. Therefore on Feb. 2, 2021, inventors herein Dr. Anne Lauren Koch, Dr. John Gatti and Dr. Walter Golub, as well as additional inventors herein Dr. Bryce Rutter, Anthony Ledwon and Cooper Preiss filed provisional patent application 63/144,942.

The digital imaging system may employ known virtual digital surgical guide overlays, used during surgery in real time, such as previously disclosed in US Patent Publication US 2002/0237486 A1 of Kopelman, entitled "Augmented Reality Enhancements for Dental Practitioners." The digital imaging system can also be used with patient CT scans being converted to 3-D virtual models of implants for positioning the implants within the patient's jaw, such as previously described in U.S. Pat. No. 8,011,927 B2 of Berckmans.

OBJECTS OF THE INVENTION

It is an object of the present invention to provide an ergonomic dental and surgical digital imaging system apparatus, which enhances the practitioner's ability to use magnification and light to their greatest capabilities, while isolating the practitioner from direct contact with the breath aerosol of the patient being treated, in a design which also promotes a healthy ergonomically correct work posture.

It is another object of the present invention to provide a method of dental and surgical imaging that enhances the practitioner's ability to use magnification and light to their greatest capabilities, while isolating the practitioner from direct contact with the breath aerosol of the patient being treated, in a design which also promotes a healthy ergonomically correct work posture.

BRIEF SUMMARY OF THE INVENTION

This updated version of an Ergonomic EZ Scope™ Digital Imaging System is actually a complete digital imaging system that combines a touchscreen computer tablet (acting as a monitor) with a digital sensor (digital camera), lens, and a diffused light source that subsequently displays a magnified image on the touchscreen computer tablet. Software associated with the tablet (acting as the input/output device for the system) along with Applicants' own proprietary software allows the programming of many functions and transforms data, such as the ability to keep the displayed images in a full focus, even when the viewing display monitor is moved toward or away from the user viewer. The software can be optionally located in the touchscreen computer tablet, or in a separate processor located elsewhere outside of the tablet.

For example, when using traditional microscopes and loupes, images increasingly go out of focus. The EZ Scope™ Digital Imaging System design corrects for the change in focal length, always keeping the image in complete focus in real time, as focal length changes. Normally, focus is diminished as images are moved farther apart from a user viewer, but the software transforms the focuses images, so that they stay in complete focus to the eyes of the viewer, no matter how close or far away the viewer is from the viewing display screen of the digital image module. The software solves this problem of maintaining focus no matter how far away from the user the digital display is located by using the optical hardware to be modified by the software, which accomplishes this unexpected data transformation of the digital image by the following steps:

The software transforms the optical images shown on the video display monitor despite movement away from the viewer and maintains image focus no matter the distance of the image from the viewer.

For example, the ability to focus at different focal lengths is due to the system having a Complementary Metal Oxide Semiconductor (CMOS sensor/lens combination) being able to support both near and far images in "static" positions due to the range of focus of our lens. In other words, the system can support a clear image both near or far in the "static" position. The user can position an optic center, or optic head, near the subject, plus four inches, and the lens will be able to focus. The user can also move the optic center, or optic head, far from the subject, plus three feet, and still be able to focus the image manually. The optic center, or optic head, also known as the optics head, includes the tablet monitor, the camera, and the fixed lens assembly.

There is no effect on image resolution over changing distances between the user and the display monitor/tablet.

The software tells the tablet to display the image from the sensor that is solely controlled by the manual use of the features of the lens (aperture and focus) and manual positioning of the optics center, or optics head, related to the subject. Once the optics center, or optics head, is in place, and the lens is adjusted for a clear image, the software allows the user to digitally zoom into the picture. This is referred to as magnification. Once the user is displaying a smaller portion of the available picture from the optic center, or optic head, the user can also move that smaller area around on the available area of the tablet. This is known as panning.

In summary, the system uses an ROI (region of interest) that is captured from the lens/sensor combination. The clarity of magnification near or far is maintained by the system's program constantly calculating (re-calculating) the changing ROI. The net effect in the changing ROI is the increase or decrease in magnification which does not affect the clarity. In other words, the optical clearness stability is maintained and does not distort during this change in ROI.

Additionally, this digital imaging system is also portable with a plug-and-play quick disconnect optical display head, that includes the touchscreen input output tablet display, camera, and fixed lens assembly, referred to herein as the optic head, from the balancing arm holding the computer tablet, i.e., monitor, camera, and fixed lens. In a preferred embodiment, the apparatus is collapsible and portable, so that specialists can take the optic head from office to office, utilizing multiple stands, resulting in a plug and play work environment. The extended maneuverability of the camera head results in simple and fast patient positioning, and the camera and display module adjust for any sit or stand ergonomic posture of the practitioner. The digital scope utilizes a high-tech lens assembly that sends an image to a very high-end digital camera, where the image can be zoomed to a magnification of 40×, all while the image stays in focus during the magnification process and also during movement of the digital image display monitor away from a first position to a more distant position, farther away from the eyes of the user. The digitized image from the camera goes to a sophisticated high-end touchscreen tablet that provides for input/output control, with the final result being a clear, focused image no matter how far or close the user viewer is to the digital image display monitor.

EZ Scope™ is a totally mobile system independent of the host organization's computer network and management systems. This discrete functionality was created to provide security, therefore HIPAA compliance for a patient's information, in this case their personal images.

It is further noted that besides having a portable base, the digital imaging system can be mounted to a surface, such as a work surface tabletop, or mounted to a wall in the vicinity of a work surface tabletop.

So, described above is the purpose of the EZ Scope™ mobile stand design which locks the Microsoft tablet from being exploited from any outside internet interferences, i.e., it is hackproof and as stated above HIPAA compliant.

The mobile design also has other unique features:
a) The lightweight optic head is composed of the tablet, CMOS camera, lens, and custom designed ring light. For example, while other tablets may be used, in one example, a Microsoft tablet may be used and while other lenses may be used, in one example, a Navitar lens may be used. It can be transported from office to office using multiple mobile stands or used in other medical, industrial, and commercial applications utilizing a fixed tabletop base.
b) USB low power proprietary control board is used for the focused ring light, CMOS camera with firmware designed to enhance EZ Scope™'s unique acquisition functions, foot pedal and power supply.
c) The custom designed weighted arm is counterbalanced which allows the optic head to remain in any position throughout its range of motion through its weight distribution and its adjustable friction screw locking joint design.
d) The tubular arm design facilitates the transmission of the power cord and has an additional USB receptacle to be utilized for image capture, both single frame and video. This eliminates beam splitting and separate video camera necessity.
e) The ergonomic ball design linkage between the tubular arm design and the optic head, and the same design between the touchscreen display and the camera/lens combination allows complete freedom of movement in all X, Y and Z axes.

f) Hands free operation for pan, zoom, etc. can be accomplished by voice recognition, touch screen, or foot pedal.
g) Red dot aiming allows centering the image before choosing to zoom or pan.

Therefore, the ergonomic digital imaging system replaces the standard microscope with binoculars for viewing images, thereby freeing the user from using his or her hands to manipulate images seen through the binoculars of the microscope. In that manner, the user can use his or her hands for other tasks, such as dental or other surgery, from a position away from the exhaled breath of the patient being treated.

An optical clearness stability is realized due to sensor/lens combination of the inventive system to support both near and far images in "static" positions due to the range of focus of our lens. In other words, the system supports a clear image both near or far in the "static" position. The optic center is positioned near the subject, plus four inches, and the lens focuses. The system also enables moving the optic center far from the subject, plus three feet, and still focus the image manually. There is no effect on the image over changing distances between the user and the monitor[tablet].

The inventive software, or application program, controls the tablet to display the image from the sensor that is solely controlled by the manual use of the features of the lens (aperture and focus) and manual positioning of the optic center related to the subject. Once the optic center is in place and the lens is adjusted for a clear image, the software allows the practitioner to digitally zoom into the image (magnification). Once the practitioner displays a smaller portion of the available picture from the optic center, the smaller area is readily moved around on the available area of the tablet (panning).

Summarizing, the system uses an ROI (region of interest) that is captured from the lens/sensor combination, where the clarity of magnification near or far is maintained by our program constantly calculating (re-calculating) the changing ROI. The net effect in the changing ROI is the increase or decrease in magnification which does not affect the clarity. In other words, the optical clearness stability is maintained and does not distort during this change in ROI.

BRIEF DESCRIPTION OF DRAWINGS

The present invention can best be understood in connection with the accompanying drawings. It is noted that the invention is not limited to the precise embodiments shown in the following drawings, in which:

FIG. 3B presents a rear view of the image display module of FIG. 3A, showing connections to the counterbalance arm for rotation, tilting, and pivot rotation for positioning the image display module by the user operator.

FIG. 3C presents a front view showing the bezel surrounding the display screen of the image display module.

FIG. 3D presents a close-up detail bottom view of the image display module, showing openings for cable access therethrough.

FIG. 4A presents a close-up detail view of the optic head connector attachable to the counterbalance arm, showing a digital module pocket for the image module and a connector, such as a button lock, or similar device, to engage a corresponding aperture in the counterbalance arm for attachment thereto.

FIG. 4B presents a view showing the display module pocket and Delrin low-friction, high wear resistant and high strength fastener components compressible around a camera ball mount for the camera.

FIG. 4C presents a side elevation view in cross section of the module arm for holding the imaging tablet and camera/lens assembly of the optic head to the counterbalance arm, where the ball mount of the camera enables about 40 degrees movement in any direction of the camera.

FIG. 9A presents a rear view of the inside of the image display module shown in FIGS. 1, 2 and 3, including the power source, and three downstream ports which can be switched ON/OFF, where the switching is controlled by software. A 45-ohm resister is shown, which has an enhanced power line up to 3 volts.

FIG. 9B presents a view of the three downstream ports of FIG. 9A.

FIG. 9C presents a perspective view of the covered downstream ports and power source of FIGS. 9A and 9B.

DETAILED DESCRIPTION OF THE DRAWINGS

Figure 1:
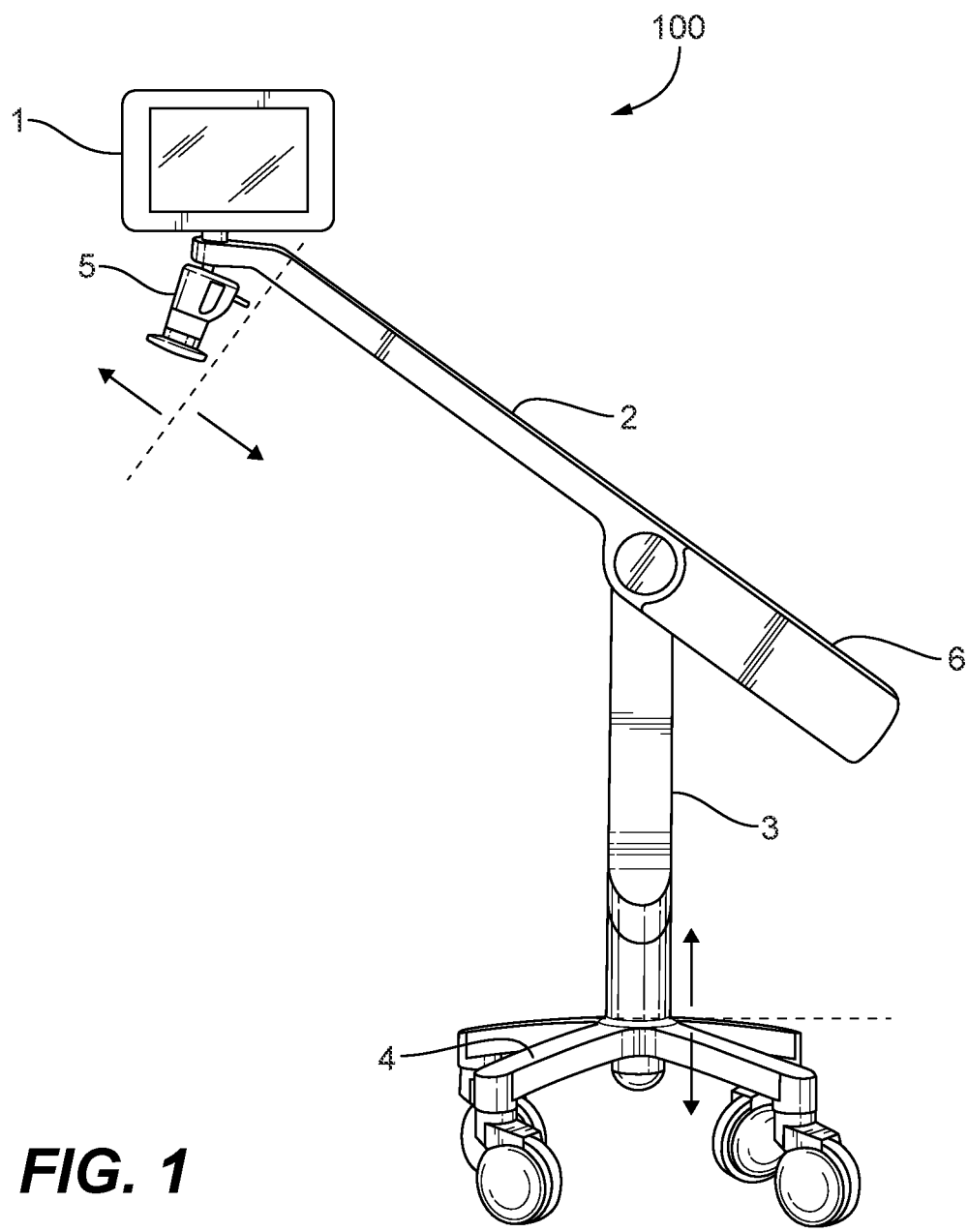
FIG. 1 presents a side perspective view of the Ergonomic EZ Scope™ Digital Imaging System of the present invention.

Overview of Concept (Modules).

As shown in drawing FIGS. 1 to 10 inclusive, the ergonomic EZ Scope™ digital imaging system consists essentially of four main modules: The imaging module (1) which is also known as the "Optic Head," can be detached from the counterbalanced arm (2, 6) integral with a four-castor base (4), which makes the unit portable. A vertical post (3) attaches to the balancing arm (2, 6) and the vertical post also attaches to the 4-caster base and assembly (4) which facilitates mobility of the unit. Camera (5) is attached to the arm (2, 6) proximate the optic head 1.

Figure 1A:
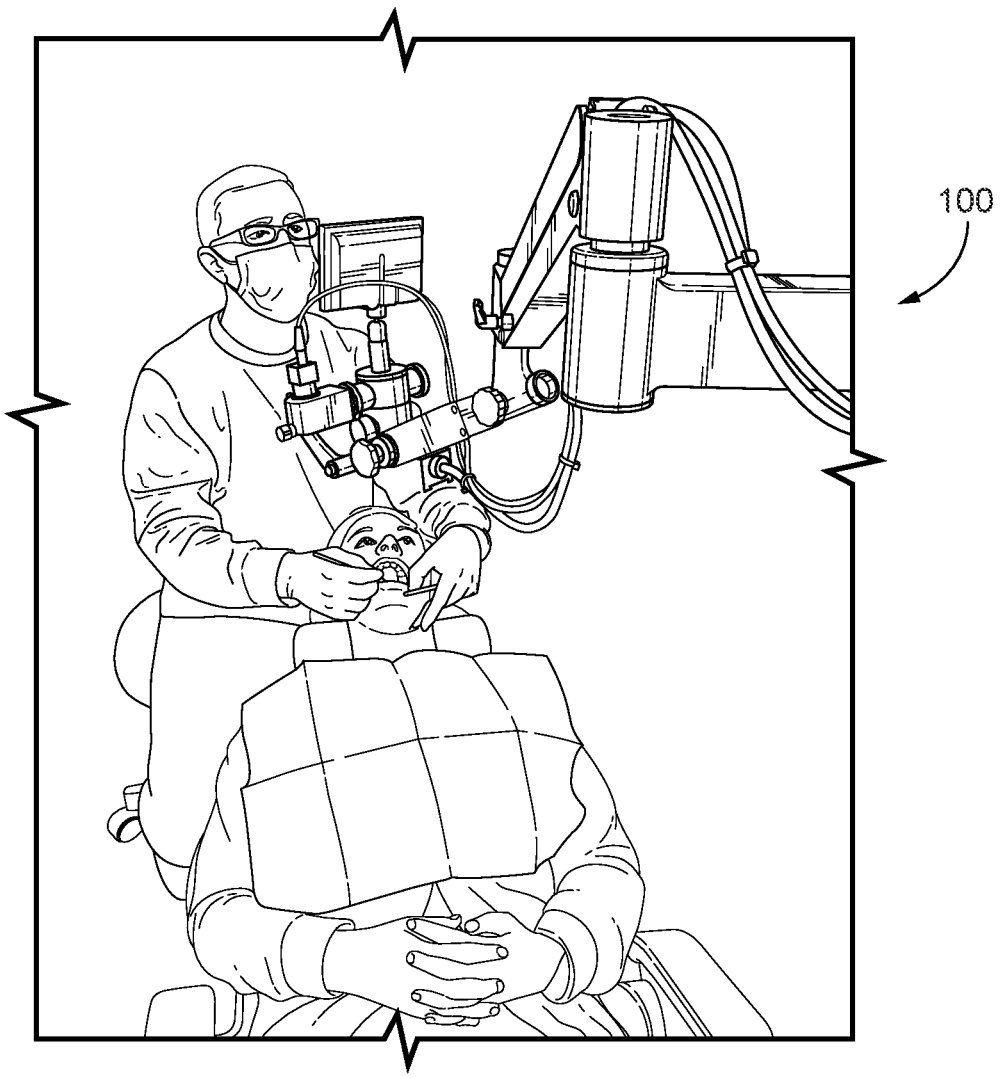
FIG. 1A presents a perspective view showing a dental or other medical practitioner sitting behind the seated patient, isolating the practitioner from direct contact with the breath aerosol of the patient being treated, in a design which also promotes a healthy ergonomically correct work posture.
Figure 2:
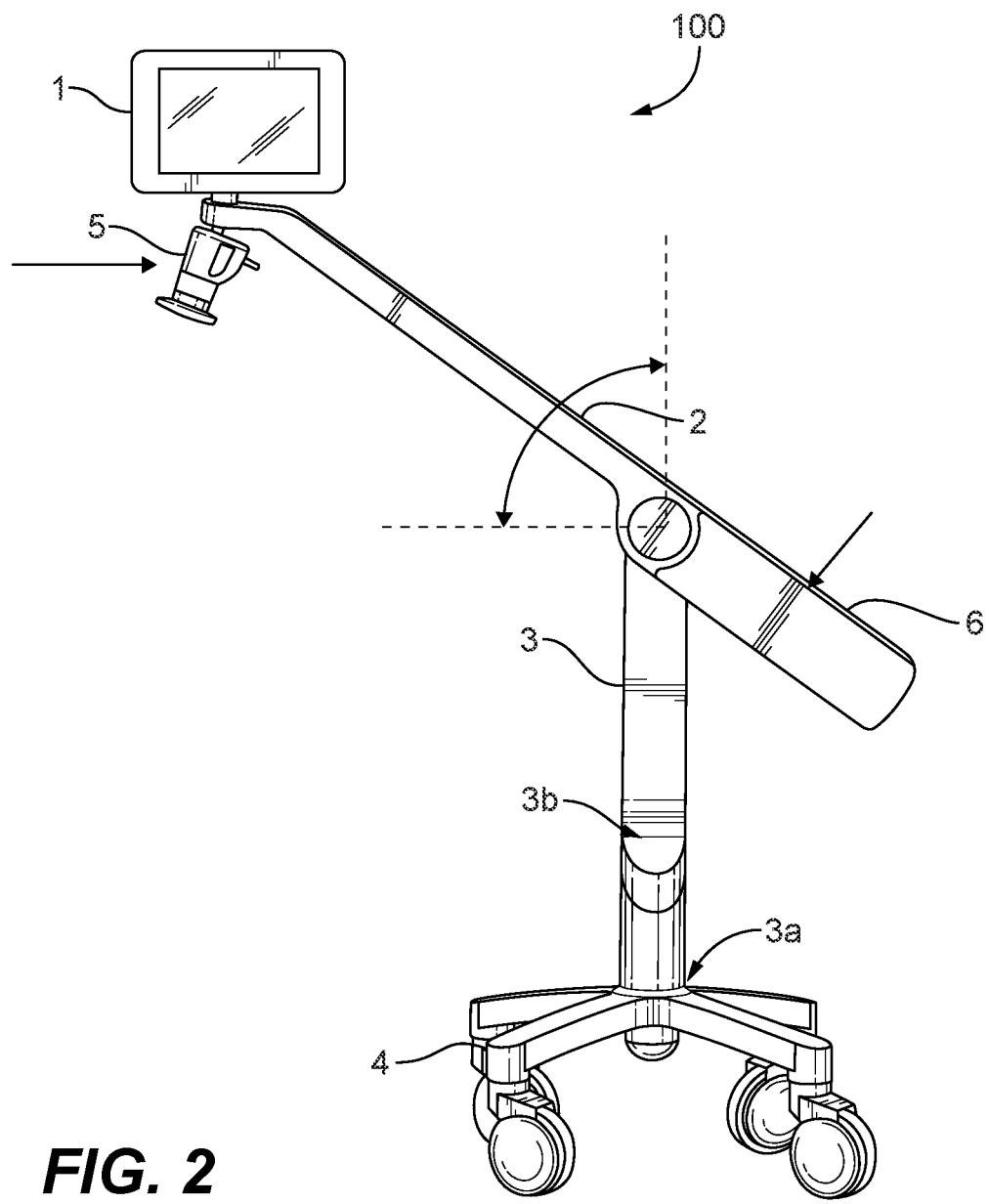
FIG. 2 presents a side perspective view of the Ergonomic EZ Scope™ Digital Imaging System as in FIG. 1, where the curved arrow line indicates the 90-degree range of motion, from a horizontal to a vertical position.

1. Overview of the Concept. As shown in drawing FIGS. 1, 1A and 2, the ergonomic EZ Scope™ is a digital imaging system (100) that allows the user to orient a digital camera (5) and image display module (1) for optimum viewing of a dentition or surgical field. FIG. 1A shows a dental or other medical practitioner sitting behind the seated patient, isolating the practitioner from direct contact with the breath aerosol of the patient being treated, using the digital imaging system (100) remotely in front of the patient, in a work environment which also promotes a healthy ergonomically correct work posture. The camera (5) is guided by hand to the desired position of viewing. The counterbalanced arm (2, 6) "follows" and holds its position via friction and counterweighting which is located at the end portion of the balancing arm (2, 6). The counterbalance arm (2, 6) has a 90-degree range of motion, from horizontal to vertical, as shown in the curved double arrow in FIG. 2. The vertical post (3) is also free to rotate on the base (4) thereby creating a point of rotation (3a), which allows for additional fine positioning. Additionally, there is an offset on the vertical post (3b) which allows clearance for the counterbalance arm (2, 6) in a vertical position.

Figure 3A:
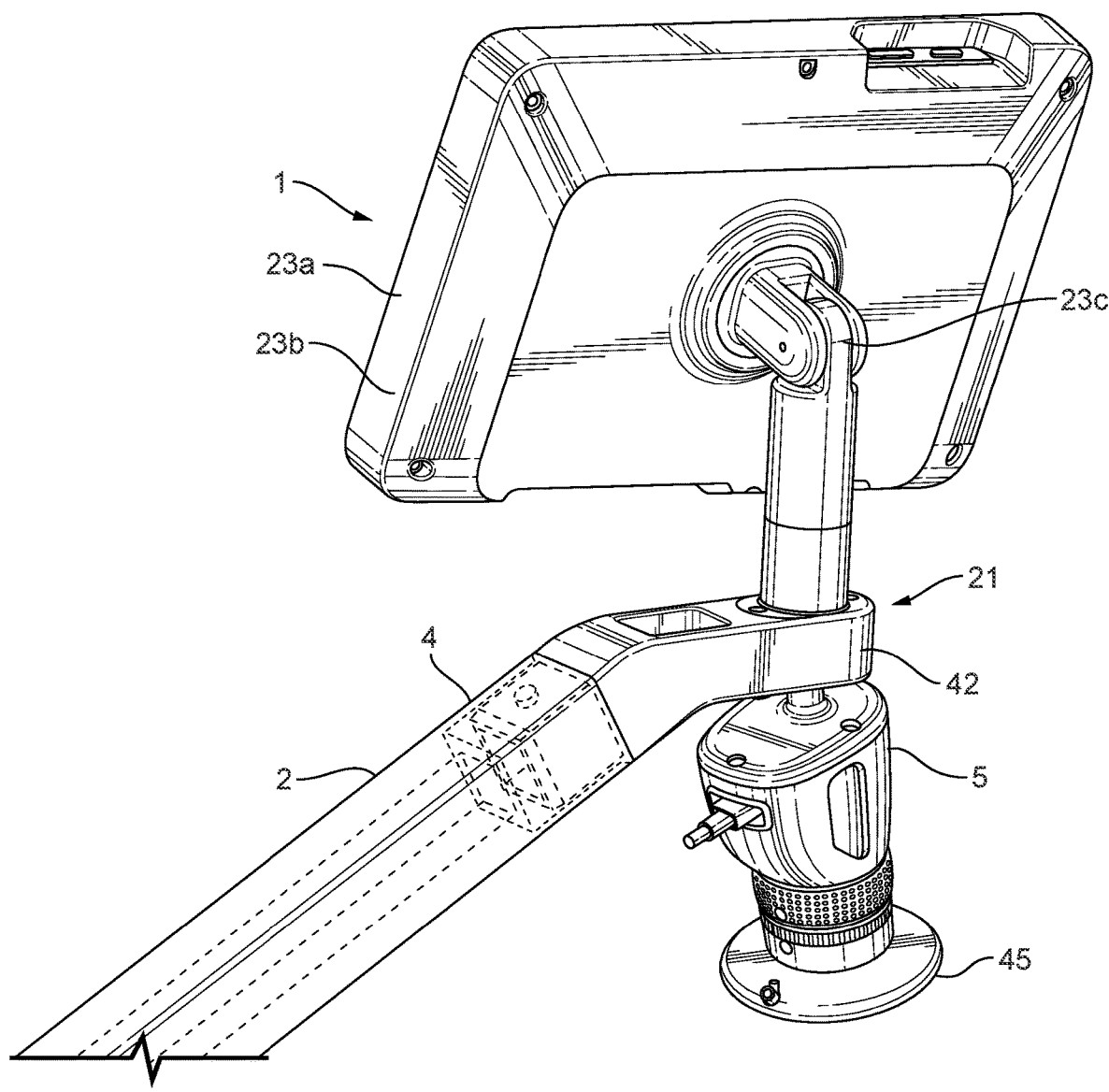
FIG. 3A presents a rear perspective view of the imaging module and camera communicating therewith, and their respective structural connections to a counterbalancing support arm.
Figure 3E:
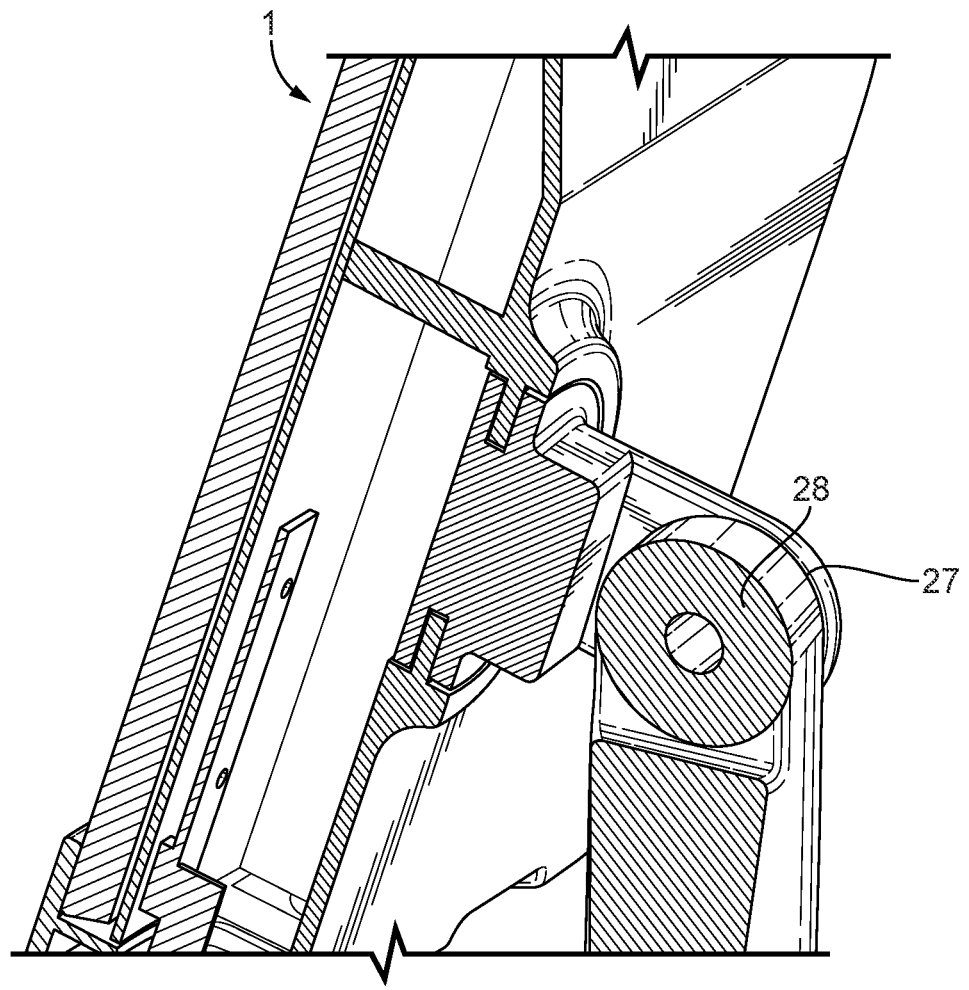
FIG. 3E presents a cross sectional side view of the image display module, showing a rear flange in the back of the bezel to facilitate rotation of the image display module.
Figure 6:
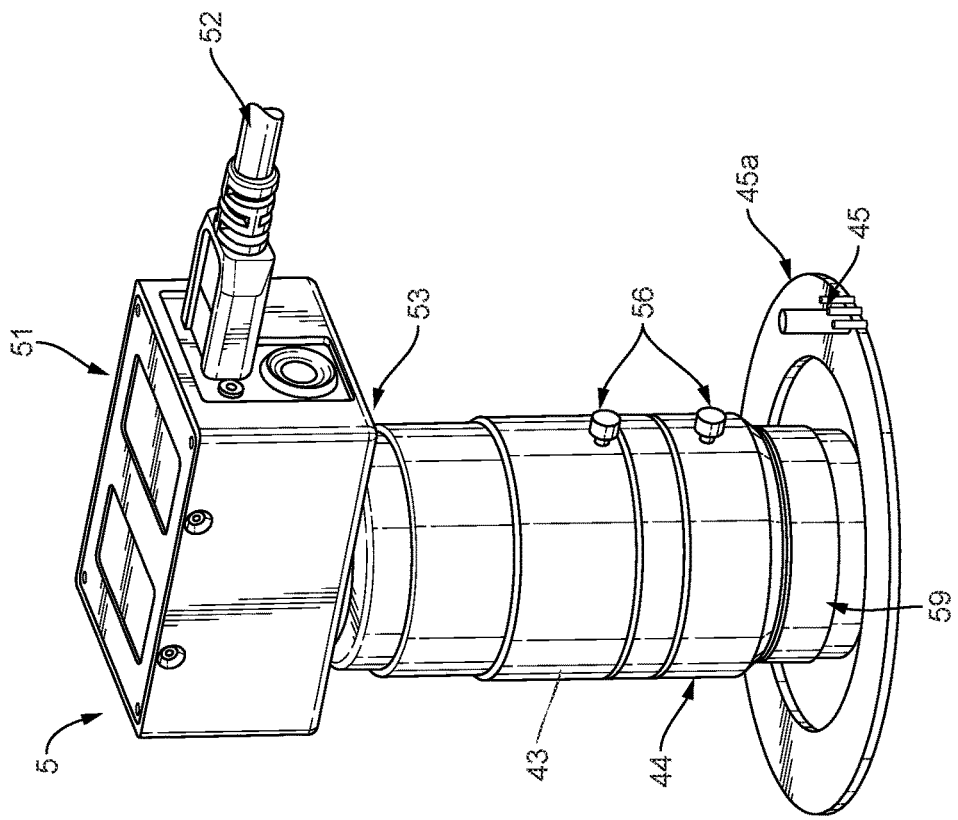
FIG. 6 presents a view of the internal components of the camera shown in FIG. 5, including its attachment to a digital sensor at an upper end and to a lower light ring and diffuser in the vicinity of the camera lens, with its aperture adjustment ring.
Figure 5:
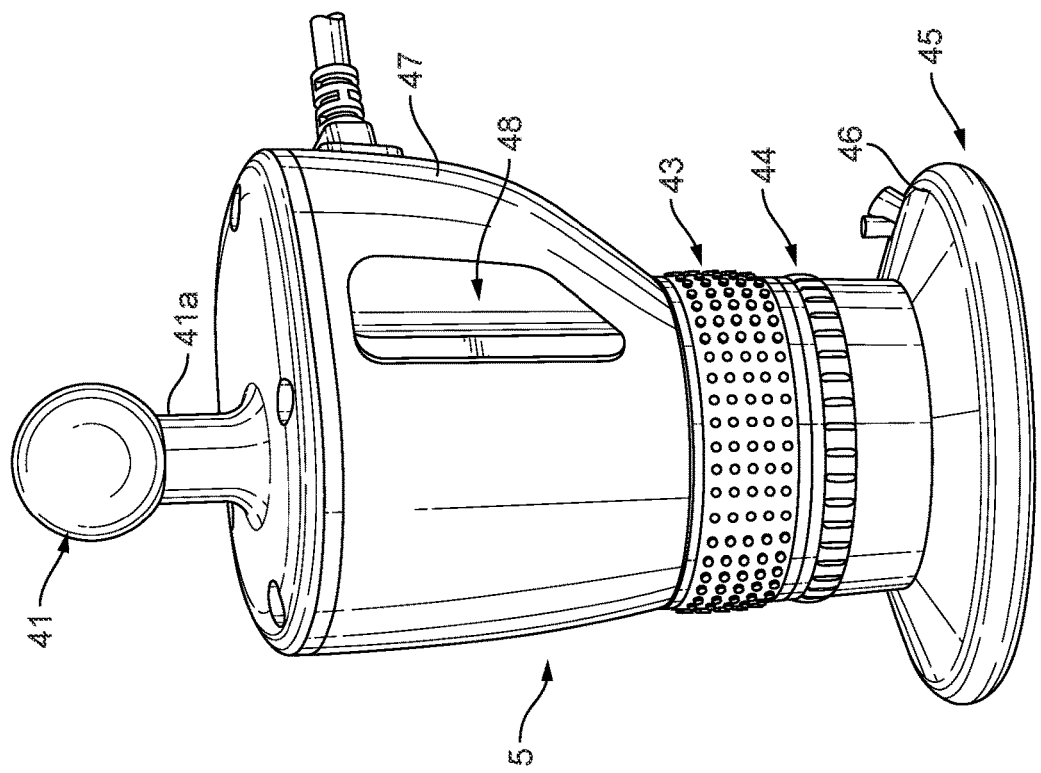
FIG. 5 presents a perspective view of the camera which is built around an existing sensor and lens component, and wherein the camera is attached to the module arm with the ball mount engageable with the module arm.
Figure 7:
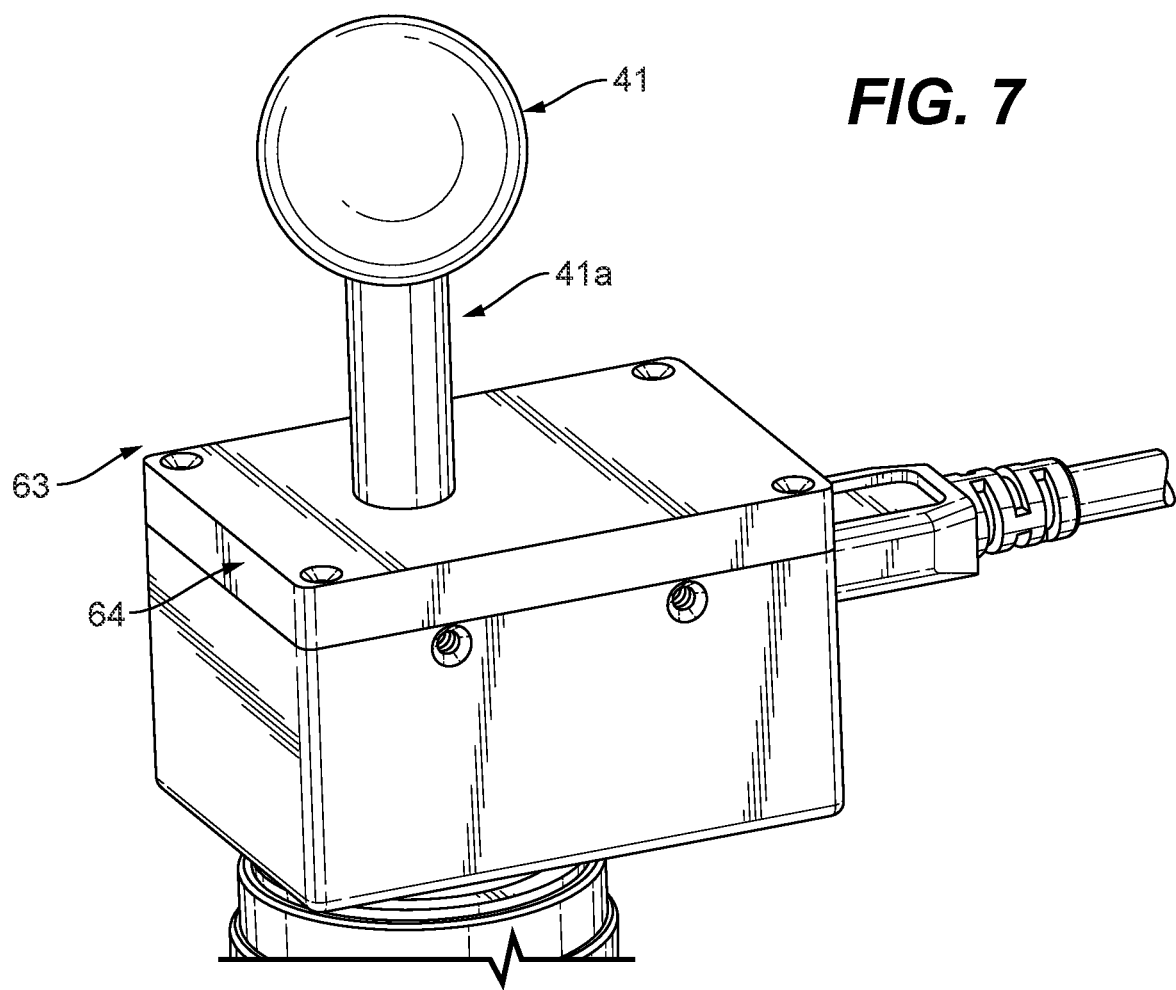
FIG. 7 presents a perspective view of the camera ball mount, wherein the ball is mounted above a vertically oriented pedestal, which attaches at an opposite end to a mounting block, from which the camera is downwardly suspended therefrom.

2. Optical Head Module Overview. As shown in drawing FIGS. 3A, 3B, 3C, 3D and 3E, the module arm (21) mounts to the counterbalance arm (2, 6) and contains hardware for the mounting of the camera-digital sensor (5) and display module (1) which may be a touchscreen computer tablet (1). The display module (1) includes the front (23a) and rear bezel (23b) and an adjustable arm (23c). The distal end of module adjustable arm (23c) includes a hollow concave nest (42) to hold a ball mount (41) of FIG. 5 for camera (5). In this figure, Applicants also see the button lock which is used to separate the balancing arm (2, 6) from the optics center, also known as the optic head, including the imaging module (1), camera (5) and lens assembly. Upon separation from the balancing arm (2, 6), the imaging module (1) will fit into a travel case (e.g., Pelican case) for safe transportation. Also, seen in FIG. 3A is the ring light and diffuser (45). Openings (26) are provided in the bottom edge (23d) of display module (1) to allow cable across therethrough, as shown in FIG. 3D. As shown in FIG. 3E, the rotate feature on the rear of the screen (1) is shown as one part but could be constructed a few different ways. An extension (27) sandwiches a circular flange (28) in the back of the bezel (23b) to provide the rotation of the screen display module (1). The rotate/tilt/pivot features of the display module (1) need to hold their position but still be movable by hand with easy forces.

3. Module Arm. As shown in drawing FIGS. 4A, 4B and 4C, the module arm (21) clips into the counterbalance arm and is detachable via a connector, such as, for example, a button lock release (33), or other connector fastener. There is a display module pocket (31a) which allows coupling to the optic head (1) (tablet). There is a built-in space (32), within the module arm (23c) to allow the passage of cables or wires therethrough. Also visible in FIGS. 4B and 4C are machined components (34, 35) which can be optionally made of DELRIN® (Acetal Homopolymer) or other functionally similar material components (34, 35), such as, for example, from San Diego Plastics or other sources, to capture and secure a camera ball mount position shown in FIG. 5. The DELRIN® or other functionally similar components (34,35) are preferably made of crystalline plastic, which offer an excellent balance of properties that bridge the gap between metals and plastics. The DELRIN®° r other functionally similar components (34,35), possess high tensile strength, creep resistance and toughness, and they also exhibit low moisture absorption. The button lock release (33), or other connector fastener, operates in such a fashion that it allows the passage of wires or cables through a hollow machined space (36).

4. Camera Overview. As shown in drawing FIG. 5, the camera (5) is built around an existing digital sensor and lens component. The camera (5) is attached to the module arm (23c) via a ball mount (41) which allows for about 40 degrees of movement from center in any direction. The ball mount (41) rotates within a concave nest (42) provided in module arm (23c) of FIG. 3A. There are adjustment rings (43,44) on the camera (5) for focus ring (43) and for aperture ring (44). Both rings (43,44) are able to fully rotate. There is additionally a ring light (45) with a diffuser which will be enclosed in a housing (46) located at the end of the lens. Over-molded touch points (48) of camera housing (47) enable a secure grip for users to position the camera (5).

5. Camera Internal Components. As shown in drawing FIG. 6, the camera components consist essentially of a digital sensor box (51) and a lens (59). A USB connector (52) delivers power and signal. Additionally, a light ring (45) with a lead wire with a length of about 18 in. will be part of the camera unit (5). It is important to note that the lens body threads into the sensor (53). Furthermore, the lens body focus ring (43) and the lens body aperture ring (44) both rotate. The rings are attached by M1 or M1.5 screws (56). Finally, the light ring (45) can be fabricated from plastic or PCB.

6. Camera Ball Mount Attachment. As shown in drawing FIG. 7, a set of metal plate screws (63) attachable to the top of the camera module are employed to create a mounting (64) for the ball mount (41) within the hollow concave nest (42) of FIG. 3A, also known as the Gatti Adaptor™ and pedestal (41a) of FIGS. 5 and 7. Specifically, ball (41) is preferably a 1-inch diameter metal ball with an internal thread of approximately ³⁄₁₆-³⁄₈. Pedestal (41a) is a threaded rod segment with matching thread specifications to the spherical ball of the ball mount (41).

Figure 8A:
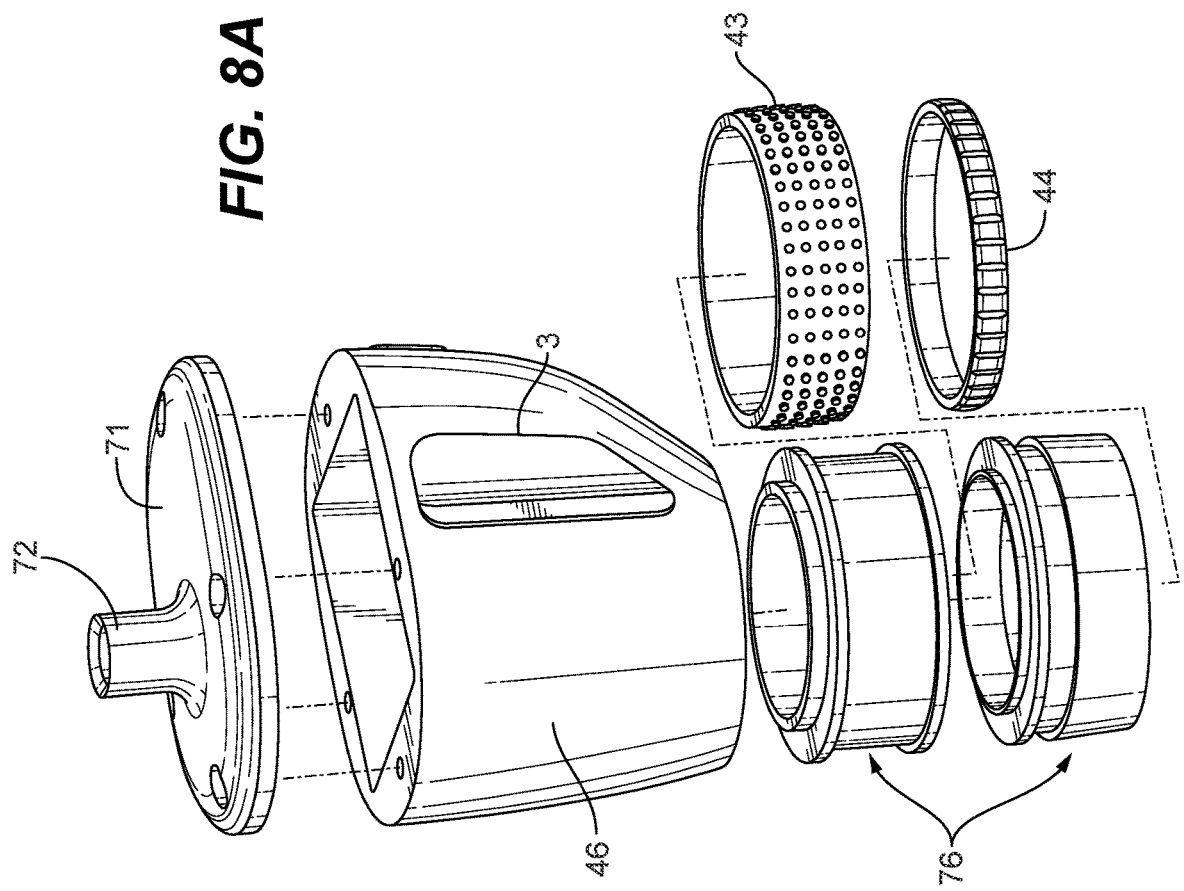
FIG. 8A presents an exploded view of the camera enclosure, which includes a hollow body having an exterior textured gripping surface and a top cap having a hollow collar to which the ball mount is attached. Manually movable focus and aperture rings extend below the hollow body.
Figure 8B:
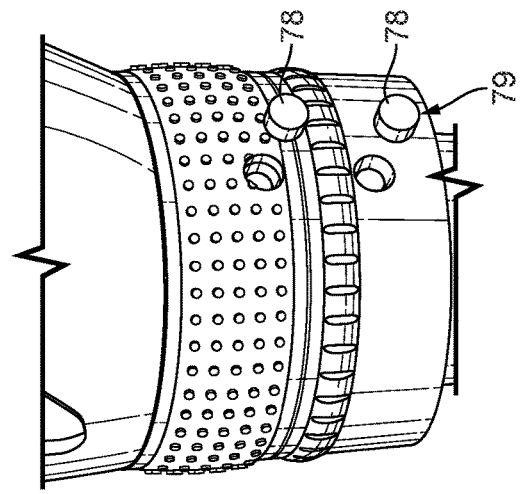
FIG. 8B presents a view of focus and aperture rings of the camera being held together by shallow fastener screws that are short enough to prevent locking of the lens component of the camera.
Figure 8E:
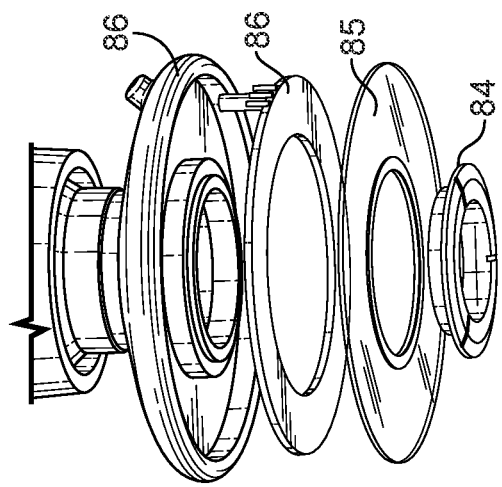
FIG. 8E presents an exploded view of the lower light ring components of the cameras align with respect to each other.
Figure 8D:
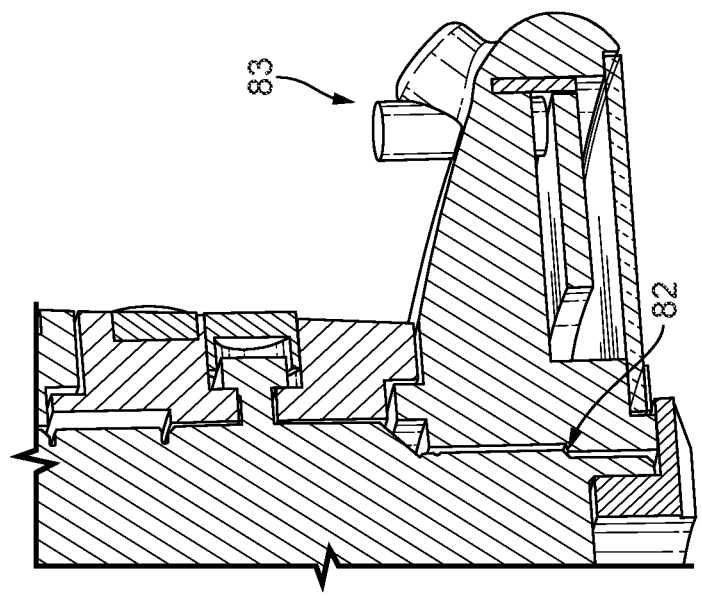
FIG. 8D presents a upside view in cross section showing a sub-housing for extending a wire therethrough so that the wire routes through an angled hole.
Figure 8C:
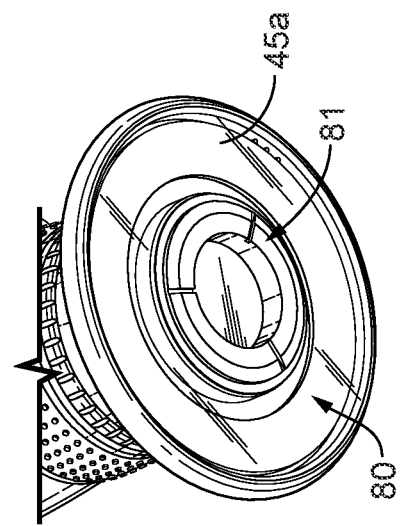
FIG. 8C presents a bottom perspective view of the non-rotatable distal bottom light ring of the camera of FIG. 8A, showing a flat translucent lens to diffuse light and a central annular fastener for attachment of the light ring to the filter ring of the camera.
Figure 8F:
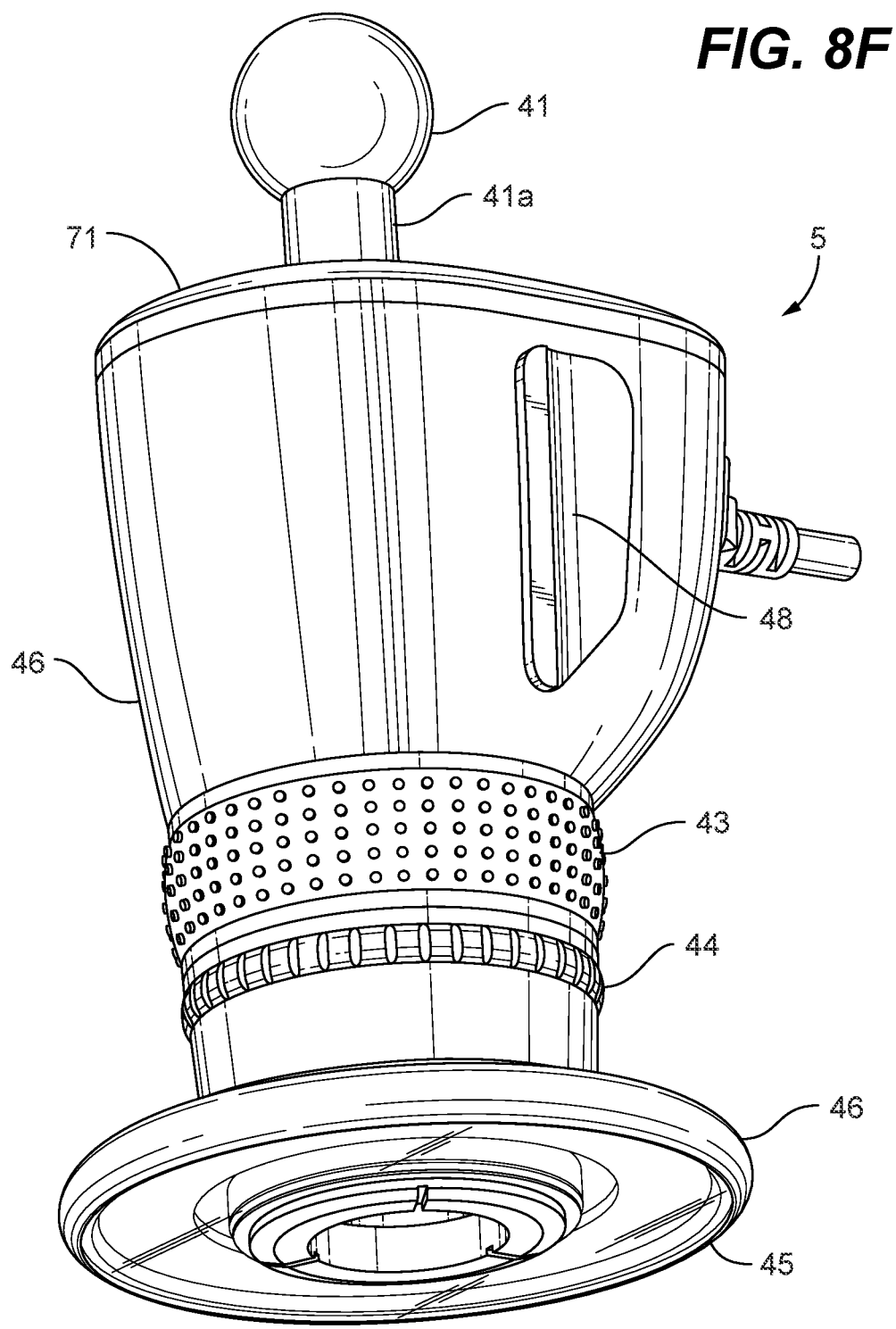
FIG. 8F presents a perspective view of the assembled camera components, with the ball mount shown at the upper end thereof.

7. Camera Enclosure. As shown in drawing FIGS. 8A, 8B, 8C, 8D, 8E and 8F, the camera components of camera (5) are inserted through the top of the camera enclosure housing (46) and captured in place with a top cap (71). The top cap (71) is intended to be held in place preferably by four M4 black oxide hex cap head screws. A flange (72) on the top cap (71) also conceals the threaded rod of ball mount (41). Also seen in FIG. 8A is an over-molded finger grip insert (48) of housing (46) as well as focus (43) and aperture rings (44) which have rubber over-molds (76) to facilitate turning capability. FIG. 8A refers to the camera enclosure housing (46). In FIG. 8B, Applicants show the screws (78) that hold the focus ring (43) and aperture ring (44) in place. The M1.5 or M2 screws (78) must be short enough that they do not lock the lens components from turning when tightened. Also included are rubber plugs (79) which conceal the screws. FIG. 8C shows from below the non-rotatable distal bottom light ring (45) of the camera (5) of FIG. 8A, showing a flat translucent lens (80) to diffuse light and a central annular fastener (81) for attachment of the light ring (45) to the filter ring (45a) of the camera (5). FIG. 8D shows a sub-housing (82) for extending a wire therethrough so that the wire routes through an angled hole (83). FIG. 8E shows the lower light ring components (84,85,86,87) of the camera (5) align with respect to each other. FIG. 8F shows the assembled camera (5) with its housing (46), top cap (71), over-molded finger grip insert (48), focus ring (43), aperture ring (44), light ring (45), as well as ball mount (41) and pedestal (41a).

Figure 9E:
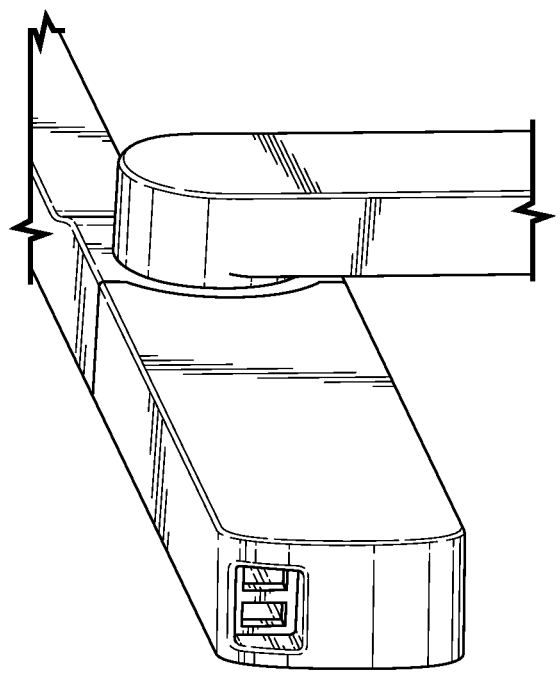
FIG. 9E presents a view of a pivoting part of the counterbalance arm showing where connector plates for the DC cord and USB cord are positioned.
Figure 9D:
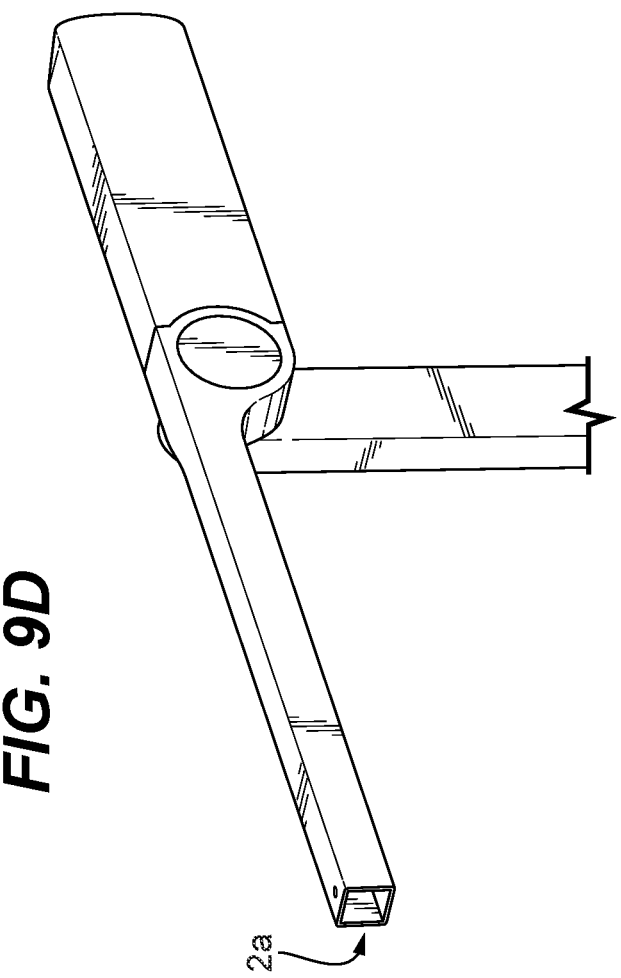
FIG. 9D presents a view a portion of the counterbalance arm showing its hollow interior of square and rectangular cross section for insertion of a DC power cord and USB cord therethrough, as well as a weighted tail for weight balancing of the counterbalance arm in a desired position.
Figure 9G:
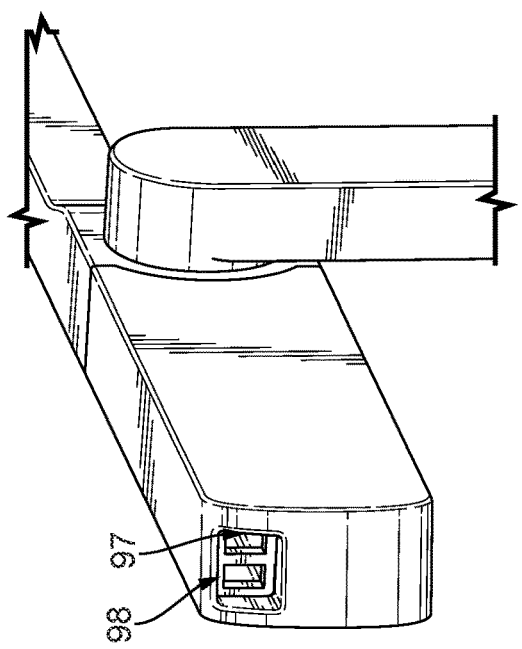
FIG. 9G presents a view as in FIG. 9E, showing links to the USB connector.
Figure 9H:
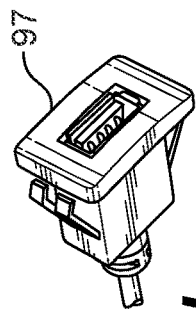
FIG. 9H presents a view of the link to the USB connector, as shown positioned in FIG. 9G.
Figure 9I:
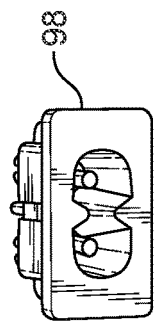
FIG. 9I presents a detail view of the link to the DC connector of FIG. 9G.
Figure 9F:
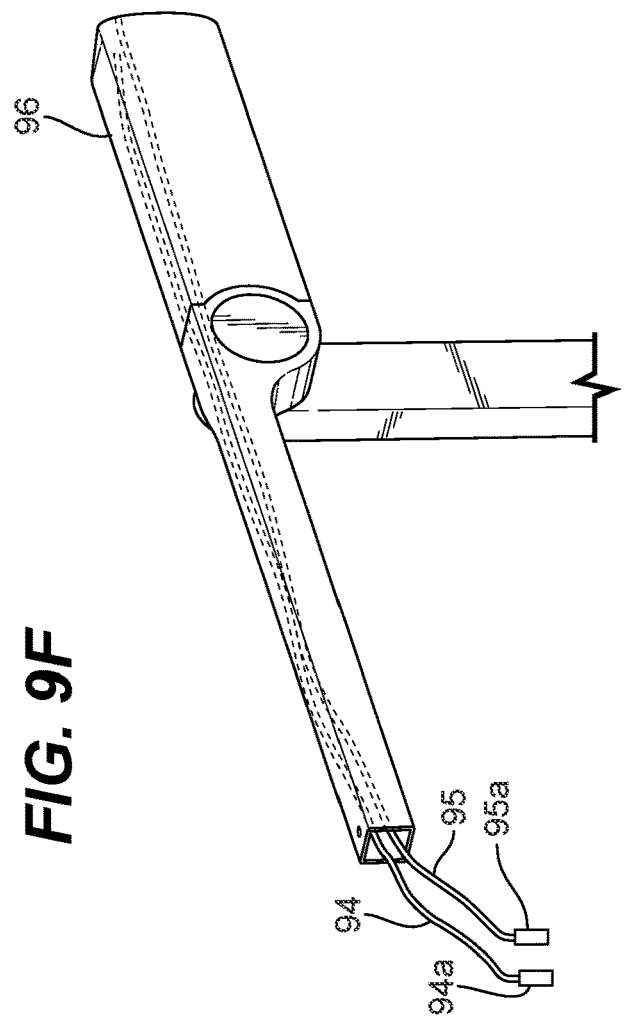
FIG. 9F presents a view of the portion of the counterbalance arm shown in FIG. 9D, showing wires cables or cords extending therethrough.

8. Display Module Internals. In FIGS. 9A, 9B. 9C, 9D and 9E, Applicants show the following: FIG. 9A shows the internal display module components of a PCB (Printed Circuit Board). Arrow (91) identifies the power source, which is preferably a 120 W Slim Surface Charger, 102 w 6.33 A Power Bank DC Charge. This is located on the back of the display module (1) monitor (tablet). Arrow (92) identifies three downstream ports (92a, 92b, 92c) for USB 3.1 and Gen 1 switchable hubs. The downstream ports (92a, 92b, 92c) can be individually switched ON/OFF. The switching is controlled by software from the host system. Switchable 5V power output port, software controlled (EZ Scope™ Software) is provided to the downstream ports (92a, 92b, 92c). Arrow (93) identifies a 45-ohm resistor with an enhanced power line up to 3 volts. FIGS. 9D and 9F show a portion of the counterbalance arm (2, 6) showing its hollow interior (2a) of square and rectangular cross section for insertion of a DC power cord (94) and USB cord (95) therethrough, as well as a weighted tail (96) for weight balancing of the counterbalance arm (2, 6) in a desired position. FIG. 9E shows a pivoting part of the counterbalance arm (2, 6), showing where connector plates for the DC cord (94) and USB cord (95) are positioned. FIG. 9F shows the portion of the counterbalance arm (2, 6) shown in FIG. 9D, showing wires cables or cords (94,95) extending therethrough. FIG. 9G shows links (97) to the USB connector (95a) of USB cord (95). FIG. 9H also shows the link (97) to the USB connector (95a) of USB cord (95), as shown positioned in FIG. 9G. and FIG. 9I shows the link (98) to the DC connector (94a) of DC cord (94) of FIG. 9G.

Figure 10:
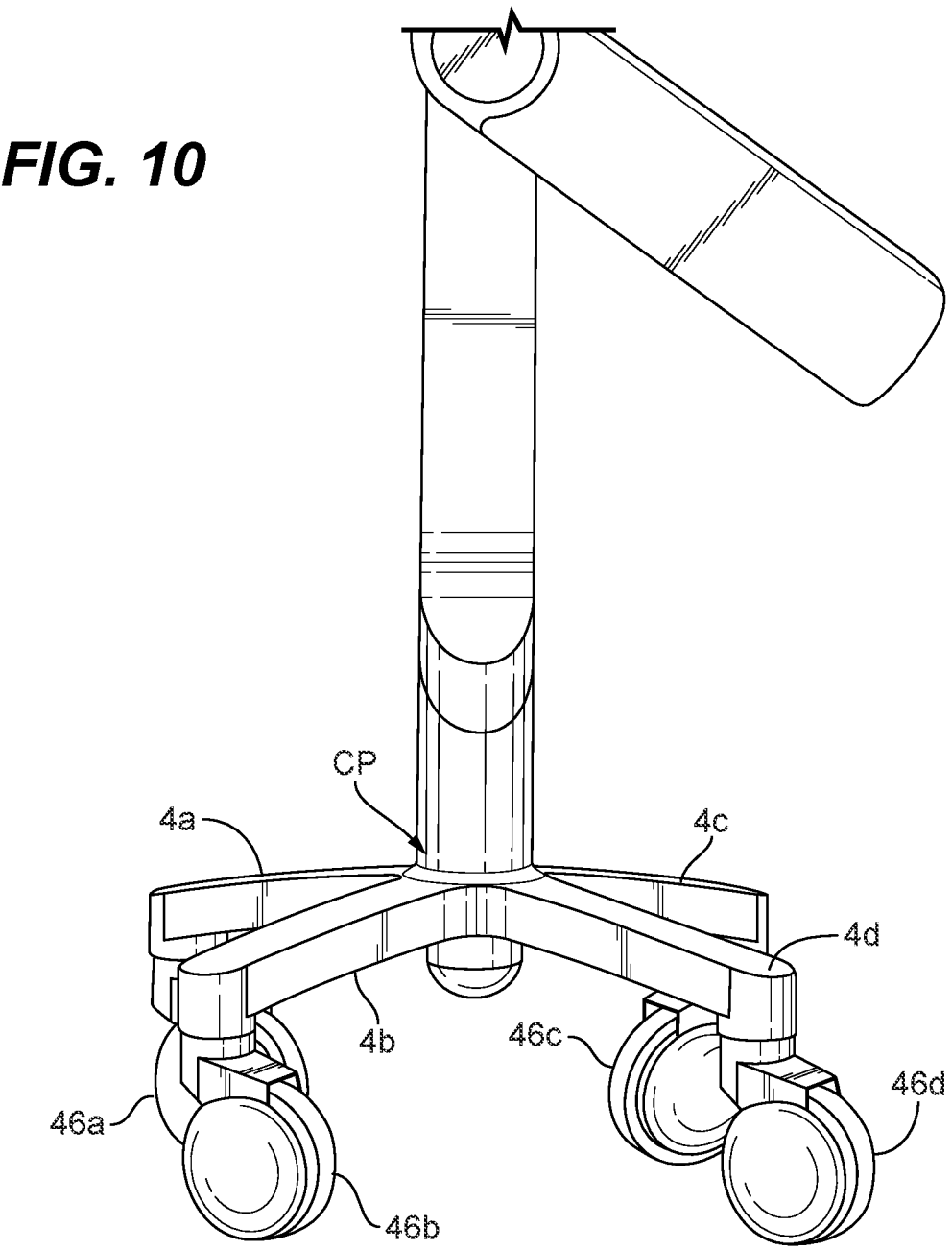
FIG. 10 presents a perspective view of the movable base and pedestal of the digital imaging system, showing a base of four arms, each attached to a rotatable movable element, such as wheels or casters, wherein the central support post is attached at a central point where the four arms meet.

9. Portable Post, Base and Casters. FIG. 10 shows the movable base (4) and vertical pedestal post (3) of the digital imaging system (100) showing base (4) of four arms (4a, 4b, 4c, 4d) as casters (4aa, 4bb, 4cc, 4dd) or wheels, wherein the vertical central support post (3) is attached at a central point (CP) where the four base arms (4a, 4b, 4c, 4d) meet. The ergonomic elements of the digital imaging system (100) can be disassembled from each other and from the base (4), and then stored and carried for re-assembly at other locations, such as at other dental surgery offices or non-medical industrial work areas.

Figure 11:
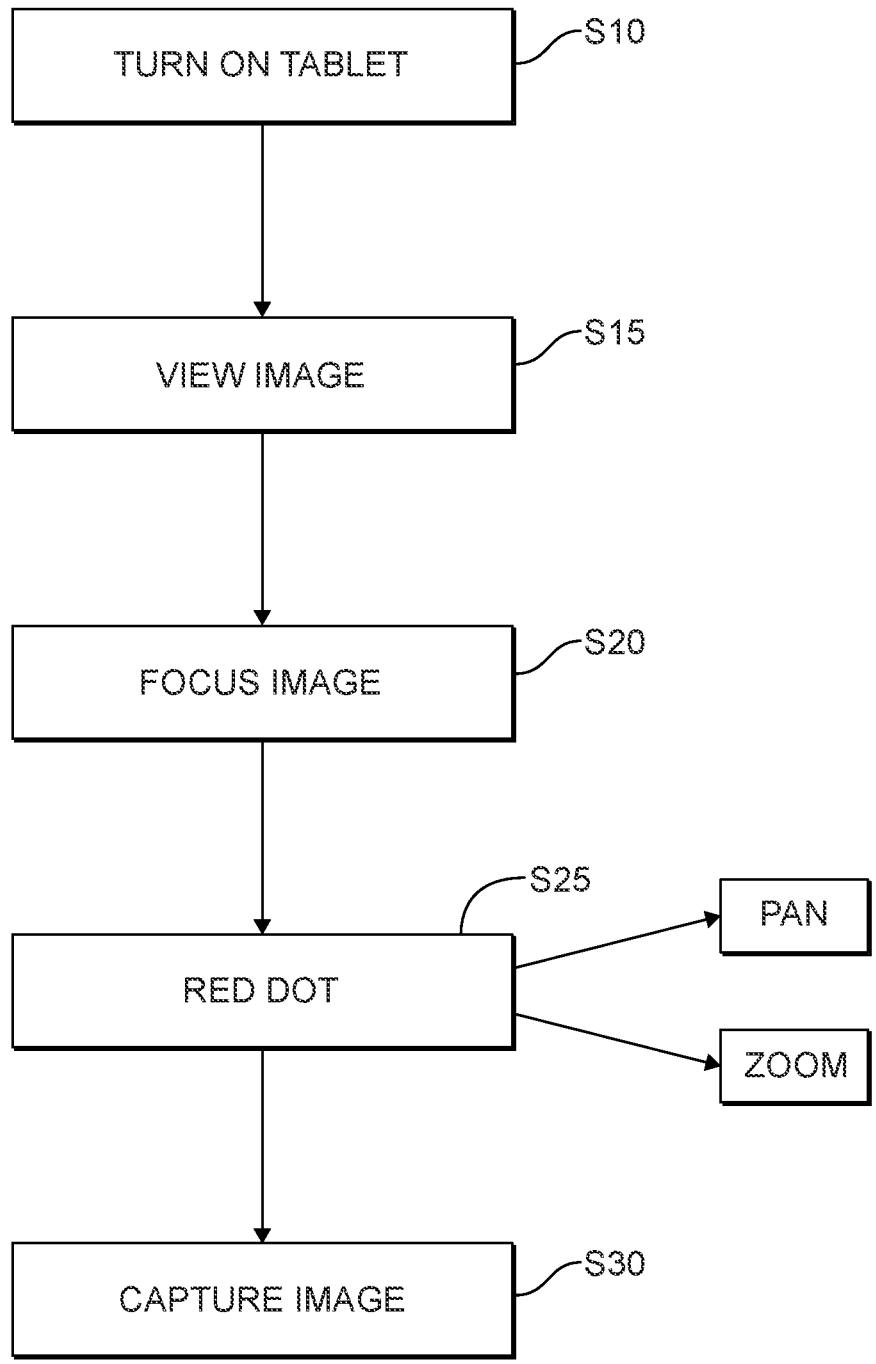
FIG. 11 presents a block diagram of the use of visual optical data in the digital imaging system.
Figure 12C:
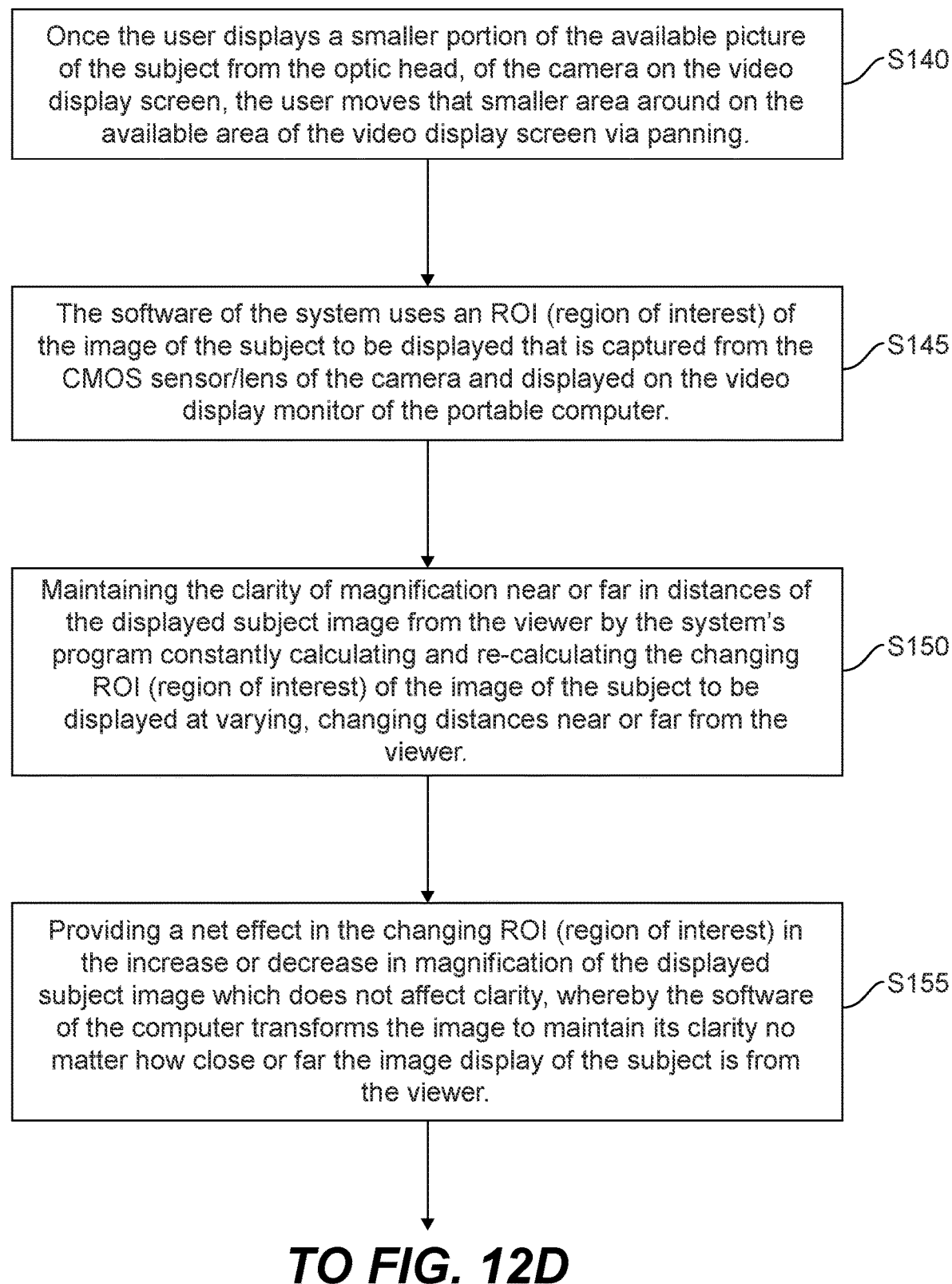
FIG. 12 presents a multipart flow chart of FIGS. 12A, 12B, 12C and 12D, illustrating the steps involved in manipulating the visual optical data.
Figure 12D:
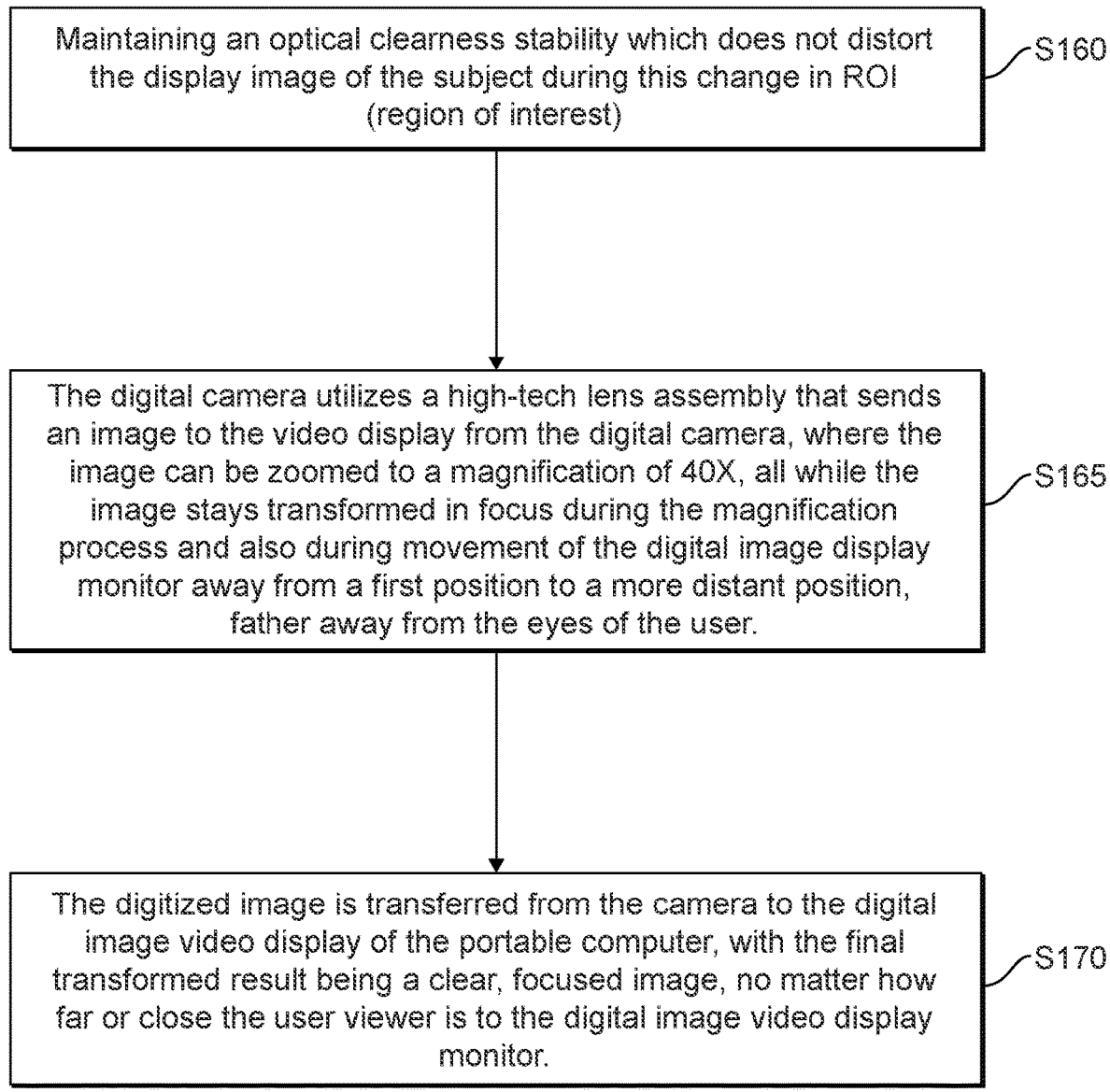

10. Software Transformation of Visual Optical Data. FIGS. 11 and 12 are flow charts that describe how the software associated with the tablet (acting as a monitor) allows the programming of many functions, and transforms data. The software or application program that implements the inventive process provides the user with the ability to keep the displayed images in a full focus, even when the viewing display monitor is moved toward or away from the user viewer. Normally, focus is diminished as images are moved farther apart from a user viewer, but the inventive software transforms the focused images, so that they stay in complete focus to the eyes of the viewer, no matter how close or far away the viewer is from the viewing display screen of the digital image module. The software solves this problem of maintaining focus no matter how far away from the user the digital display is located by using the optical hardware to be modified by the software, which accomplishes this unexpected data transformation of the digital image by the following steps.

As shown in the flowchart of FIG. 11, the user turns on the tablet to which the software is memory stored, as represented by step S10. Once operational, the software allows the user to view an image, as represented by step S15. They, the user may focus the image, as represented by step S20. Once focused, the user uses the red dot function, to pan or zoom while the image stays in focus, as represented by step S25. Then, the user may capture the focused images, as represented by step S30.

As shown in flowchart FIG. 12, the software transforms the optical images shown on the touch screen tablet display despite movement toward or away from the viewer.

For example, the ability to focus at different focal lengths is due to the system, (CMOS sensor/lens combination), which supports both near and far images in "static" positions due to the range of focus of the camera lens. Therefore, the system supports a clear image both near or far in the "static" position. The user positions the optic center, or optic head, or optic head, near the subject, and the lens will be able to focus. The user then moves the optic center, or optic head, far from the subject.

Consequently, there is no effect on the image over changing distances between the user and the display monitor/tablet.

FIG. 12 represents the inventive process, wherein the software tells the tablet to select an optical image from a camera to be displayed on a video display monitor of a portable computer. The display of the image from the sensor is solely controlled by the manual use of the features of the lens (aperture and focus) and manual positioning of the optic center, or optic head, related to the subject.

Once the optic center, or optic head, is in place, and the lens is adjusted for a clear image, the software allows the user to digitally zoom into the picture. This is referred to as magnification.

Once the user displays a smaller portion of the available picture from the optic center, or optic head, the user moves that smaller area around on the available area of the tablet. This is known as panning.

The system uses an ROI (region of interest) that is captured from the lens/sensor combination. As a result, the clarity of magnification near or far is maintained by the system's program constantly calculating (re-calculating) the changing ROI.

The net effect in the changing ROI is the increase or decrease in magnification which does not affect the clarity. The optical clearness stability is maintained and does not distort during this change in ROI.

To summarize, in FIG. 12, the digital scope utilizes a high-tech lens assembly that sends an image to a very high-end digital camera, where the image can be zoomed to a magnification of 40X, all while the image stays in focus during the magnification process and also during movement of the digital image display monitor away from a first position to a more distant position, farther away from the eyes of the user.

Therefore, as also shown in FIG. 12, the digitized image from the camera goes to a sophisticated high-end tablet, with the final result being a clear, focused image no matter how far or close the user viewer is to the digital image display monitor.

In greater detail, FIG. 12 presents another exemplary method embodiment, wherein in a first step, S100, the inventive software tells the tablet to select an optical image of a subject from a camera to be displayed on a video display monitor of a portable computer. In a step, S105, the inventive process includes providing a CMOS sensor/lens combination in the camera with the ability to focus at different focal lengths. The inventive process uses the CMOS sensor/lens combination to support both near and far images of the subject in "static" positions due to the range of focus of the camera lens, as represented by step S110. In a step S115, the inventive process adjusts the focus to support a clear image at both near or far locations of the video display monitor in a "static" position at both near and far locations of the video display monitor of the portable computer with respect to distances between the viewer of the images and the location of the video display monitor of the portable computer displaying the subject being viewed.

At a step, S120, the user positions the optic head, of the camera near the subject, and the lens is able to focus on a clear image of the subject. The user then moves the optic head, of the camera farther away from the subject, as represented by step S125. At a step S130, the software tells the portable computer to display the image from the sensor on the video display monitor of the portable computer that is solely controlled by the manual use of the aperture and focus features of the lens and manual positioning of the optic head, of the camera related to the subject being displayed at near and far distances away from the viewer. Once the optic head, of the camera, is in place at a predetermined distance from the subject, and the camera lens is adjusted for a clear image, the software allows the user to digitally zoom into the picture of the subject with magnification, as represented by step S135.

At a step S140, once the user displays a smaller portion of the available picture of the subject from the optic head, of the camera on the video display screen, the user moves that smaller area around on the available area of the video display screen via panning. The software of the system uses an ROI (region of interest) of the image of the subject to be displayed that is captured from the CMOS sensor/lens of the camera and displayed on the video display monitor of the portable computer, as represented by step S145. The software then implements a step (S150) of maintaining the clarity of magnification near or far in distances of the displayed subject image from the viewer by the system's program constantly calculating and re-calculating the changing ROI (region of interest) of the image of the subject to be displayed at varying, changing distances near or far from the viewer. At a step S155, the software implements providing a net effect in the changing ROI (region of interest) in the increase or decrease in magnification of the displayed subject image which does not affect clarity, whereby the software of the computer transforms the image to maintain its clarity no matter how close or far the image display of the subject is from the viewer.

In a step S160, the software implements maintaining an optical clearness stability which does not distort the display image of the subject during this change in ROI (region of interest). The digital camera then utilizes a high-tech lens assembly that sends an image to the video display from the digital camera, where the image can be zoomed to a magnification of 40X, all while the image stays transformed in focus during the magnification process and also during movement of the digital image display monitor away from a first position to a more distant position, farther away from the eyes of the user, as represented by a step S165. Finally, at a step S170, the digitized image is transferred from the camera to the digital image video display of the portable computer, with the final transformed result being a clear, focused image, no matter how far or close the user viewer is to the digital image video display monitor.

DETAILED DESCRIPTION OF THE INVENTION

The EZ Scope™ subject matter is actually a complete digital imaging system. Instead of looking through binoculars, as is common with a surgical operating microscope, the clinician looks at a monitor which is a sophisticated computer tablet. The software with the tablet is also its latest version accompanied by the inventor's proprietary software. This combination of the binoculars and the software enable implementation of many functions. The optic center, or optic head, combines a digital sensor with a very sophisticated lens and also contains the obligatory light source and diffuser.

Because of a special ball-swivel adapter, (known as the tradename the "Gatti adaptor"), the optic center, or optic head, has incredible maneuverability which makes patient positioning quite easy. This is significant improvement because very often with surgical operating microscopes, the patient has to lie on their side. Since it is completely digital, there is no need to par focal anything with the ergonomic EZ Scope™ digital imaging system. The need to par focal is the biggest challenge associated with a surgical operating microscope.

When using the ergonomic EZ Scope™ Digital Imaging System the user can Zoom up in magnification to approximately 20× and remain in focus. Furthermore, Applicants employ a Bluetooth technology, to Zoom in or Zoom out, and Pan left or Pan right, which allows the user to view the entire field. In this new version of the ergonomic digital EZ Scope™, Applicants have already programmed in voice recognition to Zoom in, Zoom out, Pan left, Pan right, etc.

As a result of the sophisticated software associated with the tablet, along with our proprietary software that Applicants have built into the ergonomic EZ Scope™ Digital Imaging System, which enables implementation of the inventive method of use, Applicants can display surgical stents of implant placement and other complicated procedures. A user can simply turn on the scope and the user can have a red dot function that allows the user to place the red dot over a target area, ROI. Then, then the user simply uses a Zoom feature to enlarge the image up to whatever magnification the user needs. The touchscreen tablet displays a surgical stent, which may be a video image of a tangible surgical installed in real time over the mouth gum area being treated, or it may be in fact a conventional virtual digital overlay of a virtual surgical guide positioned virtually in real time over the image of the mouth gum area being treated.

Furthermore, the disinfection protocol associated with the EZ Scope™ Digital Imaging System is simple. No more plastic bags are needed for covering SOM's. A staff member simply wipes it down with Applicants' proprietary disinfectant, "Glacier Blue," that kills all virus in 42 seconds. For example, in a preferred embodiment, Applicants have worked with Vermont Soap Company and have created a colored disinfectant, "Glacier Blue" that in addition to killing all viruses, also cleans glass and screens (tablets, computers, etc.) well. A unique and proprietary aspect of Glacier Blue is that one can actually see where one places it and, of course, it can used on all surfaces, not just the EZ Scope™ Digital Imaging System. It is also organic.

Applicants have made the digital EZ Scope™ Digital Imaging System completely portable. As more dentists (especially dental specialists) and other health care providers, work in multiple offices Applicants have made the optic head of the EZ Scope™ Digital Imaging System fully portable. At the end of the day, the doctor simply removes the optic center, or optic head, by engaging a simple one touch disconnect design and places it into the EZ Scope™ Digital Imaging System custom designed travel case for easy and safe transportation. He or she then goes to a different office and simply connects the digital optic center, or optic head, to the stand assembly which that office has purchased.

Another application of the use of the EZ Scope™ Digital Imaging System is in the field of commercial and industrial inspection and quality control, and medical labs and other surgical applications. Among various uses, the EZ Scope™ digital imaging system can be utilized in the inspection of circuit boards, semi-conductor, or similar technology, and even munitions. The design can also be used in medical research laboratories to replace traditional microscopes and surgical applications that currently use microscopes. One of the aspects of the EZ Scope™ Digital Imaging System that makes it particularly well suited to these tasks is its ability to extend the focal length and still have the image of the subject being studied to remain in focus. The focal length of the EZ Scope™ Digital Imaging System can be extended easily to a distance of three-four feet, which is more than adequate to allow the inspecting technician to use their hands when observing the image on the monitor. The is a significant differentiation from traditional binocular microscopes which routinely have a very short focal length of a few inches (approximately 4-7 inches). This shorter focal length does not allow the inspecting technician to work with their hands in a user-friendly, ergonomic manner. It is further noted that besides having a portable base, the digital imaging system can be mounted to a surface, such as a work surface tabletop, or mounted to a wall in the vicinity of a work surface tabletop.

In an alternate embodiment and product line extension based on the same platform EZ Scope™ Digital Imaging System can be used use in beauty or nail salons, the beauty salon version has a display monitor, but without the sophisticated software of a high-end tablet for maintaining focus clarity no matter how near or far the monitor is located. The scaled down version means basically the same concept as the preferred embodiment as shown in FIGS. 1-8F, 10, but with less expensive component parts, and not with the sophisticated image clarity features of FIGS. 9A-9I and flowcharts 11 and 12. For example, instead of Zooming to 25×-40×, the scaled down model zooms to a maximum of about 10-12×. Instead of a high-end digital sensor and Microsoft tablet, it has instead a very economical monitor and a simple camera. The lens would also be downgraded to very simple. But the scaled down model for beauty or nail salons can have some similar features such as the Zoom of the customers face, hands, or toes being treated by an aesthetician at the beauty or nail salon. It is further noted that besides having a portable base, the digital imaging system can be mounted to a surface, such as a work surface tabletop, or mounted to a wall in the vicinity of a work surface tabletop.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended claims.

We claim:

1. A digital imaging system, comprising:
   a base;
   a counterbalanced arm with a proximal and a distal end, where the counterbalanced arm is connected to the base;
   a digital image display screen device mounted at a first mounting location on the proximal end of the counterbalanced atm;
   a digital camera pivotally mounted at a second mounting location on the proximal end of the counterbalanced arm; said digital image screen device mounted on and with rotate/tilt/pivot features above said digital camera;
   a controller for controlling said digital image display screen device and said digital camera;

wherein the distal end of the counterbalanced arm has a counterweighted proximal end portion pivotally mounted to the base to allow a 90-degree range of motion;

wherein said digital camera includes a lens portion surrounded by a ring light with a diffuser for lighting up a surgical field; and wherein the controller controls said digital image display screen device and said digital camera to maintain displayed images in a full focus even where said digital image display screen device and said digital camera are moved toward or away from said surgical field; and said digital image display screen device of said imaging system replacing a standard microscope with binoculars for viewing images, thereby freeing a dental dental/medical practitioner from using his or her hands to manipulate images seen through the binoculars of the microscope, whereby the dental dental/medical practitioner can use his or her hands for other dental dental/medical surgical tasks, from a position away from the exhaled breath of the patient being treated.

2. The digital imaging system as in claim 1, wherein the counterbalanced arm further comprises a first ball mount for supporting and allowing rotation of said module arm and wherein the first ball mount is located on said counterbalanced arm between said digital imaging display screen device and said digital camera.

3. The digital imaging system as in claim 2, further comprising a vertical post extending up from said base to connect said base to said counterbalanced arm.

4. The digital imaging system as in claim 3, wherein the counterbalanced arm includes a counterweighted distal having a 90-degree range of motion using friction for holding any selected position within its range of motion, said base and wheel assembly providing portability for said digital imaging system; and wherein said digital camera has a lens portion surrounded by said ring light with a diffuser for lighting up a surgical field, and over-molded touch points for a user the dental/medical practitioner to position said digital camera.

5. The digital imaging system as in claim 1, wherein said digital imaging display screen device displays said surgical field.

6. The digital imaging system as in claim 5, further comprising means for keeping displayed images in a full focus even when said module arm carrying said digital camera is moved toward or away from said surgical field.

7. The digital imaging system of claim 6, wherein said means for keeping displayed images in a full focus comprises software.

8. The digital imaging system of claim 7, wherein said system is adapted to operate independently of a host organization's computer network and/or computer management systems, thereby being free of any outside internet interferences, notably being hackproof and HIPAA compliant.

9. The digital imaging system of claim 8, wherein said monitor is a laptop computer.

10. The digital imaging system of claim 8, wherein the distal end of said module arm includes a hollow concave nest holding a second ball mount for said digital camera allowing about 40 degrees movement in any direction of said digital camera.

11. The digital imaging system of claim 10, wherein said digital camera is enclosed within a housing with a top opening enclosed by a top cap having an opening for a threaded rod supporting said second ball mount outside of housing, a lens opening for said digital camera being on an underside of said housing.

12. The digital imaging system of claim 7, wherein said digital camera has a zooming capability of 40×, said software maintaining focus during magnification.

13. The digital imaging system of claim 1, wherein said base is a movable base with a wheel/caster assembly for providing portability of said digital imaging system.

14. The digital imaging system of claim 1, wherein said base is a mount to a surface.

15. The digital imaging system of claim 1, further comprising said digital image display screen device having image panning software.

16. The digital imaging system of claim 1, further comprising an optical stability component preventing distortion of the display image of any part of said surgical field during any change of region of interest.

17. The digital imaging system of claim 1 further comprising application program that when operated upon by a computer processor implements the following steps:

selecting an optical image of a subject from said digital camera to be displayed on said digital image display screen device of said digital imaging system having said portable computer;

in reliance upon a CMOS sensor/lens combination in said digital camera, said digital camera focusing on an image with objects therein located at different focal lengths.

18. The digital imaging system of claim 1, further comprising said application program controlling said digital camera for focusing supporting both near and far images of the subject in "static" positions due to the range of focus of said digital camera lens.

19. The digital imaging system of claim 18, further comprising said application program controlling said digital camera for adjusting the focus of an image to support a clear image at both near or far locations of said digital image display screen device of said digital imaging module in respective "static" positions at both near and far locations of said digital image display screen device of the portable computer of said digital imaging system, with respect to distances between the viewer of said digital images and the location of said digital image display screen device of the portable computer of said digital imaging system, displaying the subject being viewed.

20. The digital imaging system of claim 19, further comprising said optic lens of said digital camera having an optic lens of said digital camera being positionable near the subject at a first predetermined distance so that said optic lens is able to focus on a clear image of the subject;

said optic lens of said digital camera being movable farther away from the subject; at a second predetermined distance;

wherein said application program instructs said digital image display screen device of the portable computer of said digital imaging system to display the image from the sensor on said digital image display screen device of the portable computer of said digital imaging system, that is solely controlled by the manual use of the aperture and focus features of the optic lens of said digital camera, and manual positioning of the optic lens of said digital camera, related to the subject being displayed, at said first predetermined near distance and subsequent predetermined far distances away from the viewer.

21. The digital imaging system of claim 20, wherein upon positioning the optic lens of said digital camera is in place at said first predetermined distance from the subject, and said digital camera lens being adjustable for a clear image, the application program allowing the user dental/medical practitioner to digitally zoom into the picture of the subject with magnification; and wherein upon displaying a smaller portion of the available picture of the subject from the optic lens of said digital camera on said digital image display screen device of the portable computer of said digital imaging system, and a panning component permitting the movement of the smaller area around on the available area of said digital image display screen device of the portable computer of said digital imaging system.

22. The digital imaging system of claim 21, further comprising said digital camera capturing a ROI (region of interest) of the image of the subject to be displayed that is captured from the CMOS sensor/lens of said digital camera and displaying the ROI on said digital image display screen device of the portable computer of said digital imaging system;

said digital camera maintaining the clarity of magnification near or far in said first and second predetermined distances of the displayed subject image from the viewer by said digital imaging system's program, and constantly calculating and re-calculating the changing ROI (region of interest) of the image of the subject to be displayed at varying, changing subsequently predetermined distances near or far from the viewer; and said digital camera providing a net effect in the changing ROI (region of interest) in the increase or decrease in magnification of the displayed subject image which does not affect the clarity, whereby the application program transforms the image to maintain its clarity no matter how close or far the image display of the subject is from the viewer.

23. A method for a dental/medical practitioner conducting a dental/medical procedure comprising the steps of:

placing a mobile digital imaging system including a digital camera adjacent a surgical field inside a surgery field of a patient for viewing and displaying said surgical field on a screen;

said dental/medical practitioner positioning himself or herself behind said patient, said screen being positioned so that said dental/medical practitioner can view said surgical field; and said screen being mounted directly with rotate/tilt/pivot features on and above said digital camera; and said dental/medical practitioner using his or her hands for conducting said dental/medical procedure relying on images on said screen of said digital imaging module, whereby said dental/medical practitioner is isolated from direct contact with breath aerosol of the patient being treated; said screen of said imaging module replacing a standard microscope with binoculars for viewing images, thereby freeing the dental/medical practitioner from using his or her hands to manipulate images seen through the binoculars of the microscope, whereby the dental practitioner can use his or her hands for other dental/medical surgical tasks, from a position away from the exhaled breath of the patient being treated.

* * * * *